United States Patent
Rademann et al.

(10) Patent No.: US 10,683,286 B2
(45) Date of Patent: Jun. 16, 2020

(54) FURAZAN-3-CARBOXYLIC ACID DERIVATIVES AND USE THEREOF IN TREATMENT OF CANCER

(71) Applicant: FREIE UNIVERSITAET BERLIN, Berlin (DE)

(72) Inventors: Joerg Rademann, Berlin (DE); Ee Lin Wong, Berlin (DE); Christoph Arkona, Leipzig (DE); Boo Geun Kim, Berlin (DE); Eric Nawrotzky, Berlin (DE)

(73) Assignee: FREIE UNIVERSITAET BERLIN, Berlin (DE)

( * ) Notice: Subject to any disclaimer, the term of this patent is extended or adjusted under 35 U.S.C. 154(b) by 0 days.

(21) Appl. No.: 16/338,627

(22) PCT Filed: Oct. 5, 2017

(86) PCT No.: PCT/EP2017/075394
§ 371 (c)(1),
(2) Date: Apr. 1, 2019

(87) PCT Pub. No.: WO2018/065536
PCT Pub. Date: Apr. 12, 2018

(65) Prior Publication Data
US 2019/0382392 A1 Dec. 19, 2019

(30) Foreign Application Priority Data

Oct. 5, 2016 (EP) ..................... 16192394

(51) Int. Cl.
C07D 413/12 (2006.01)
A61K 31/4245 (2006.01)

(52) U.S. Cl.
CPC ........ *C07D 413/12* (2013.01); *A61K 31/4245* (2013.01)

(58) Field of Classification Search
CPC ............. C07D 413/12; A61K 31/4245
See application file for complete search history.

(56) References Cited

U.S. PATENT DOCUMENTS

2012/0190708 A1  7/2012 Mackerell et al.

FOREIGN PATENT DOCUMENTS

CN  102610998 B    4/2013
WO  WO2011006158  * 1/2011

OTHER PUBLICATIONS

International Search Report mailed in PCT/EP2017/075394 dated Dec. 15, 2017.
Mizuki et al.: "Flt3 mutations from patients with acute myeloid leukemia induce transformation of 32D cells mediated by the Ras and STAT5 pathways", Blood 2000, 96, 3907-3914.
Kindler et al.: "FLT3 as a therapeutic target in AML: still challenging after all these years", Blood 2010, 116, 5089-5102.
Dae-Seop Shin et al: "Synthesis, modeling, and crystallographic study of 3,4-disubstituted-1,2,5-oxadiazoles and evaluation of their ability to decrease STAT3 activity", Medchemcomm, vol. 1, No. 2, Jan. 1, 2010 (Jan. 1, 2010), p. 156.
Brent D. G. Page et al: "Small Molecule STAT5-SH2 Domain Inhibitors Exhibit Potent Antileukemia Activity", Journal of Medicinal Chemistry, vol. 55, No. 3, Feb. 9, 2012.
Pallandre Jean-Rene et al: "Novel aminotetrazole derivatives as selective STAT3 non-peptide inhibitors", European Journal of Medicinal Chemistry, vol. 103, Sep. 1, 2015.
Rondanin Riccardo et al: "Inhibition of activated STAT5 in Bcr/Abl expressing leukemia cells with new pimozide derivatives", Bioorganic & Medicinal Chemistry Letters, Pergamon, Amsterdam, NL, vol. 24, No. 18, Aug. 1, 2014.
European Search Report mailed in EP 16192394.1 dated Jan. 4, 2017.

* cited by examiner

*Primary Examiner* — Karen Cheng
(74) *Attorney, Agent, or Firm* — Fox Rothschild LLP

(57) ABSTRACT

A furazan-3-carboxylic acid derivative or pharmaceutically acceptable salt thereof for treatment of acute myeloid leukemia.

16 Claims, 13 Drawing Sheets

FURAZAN-3-CARBOXYLIC ACID DERIVATIVES AND USE THEREOF IN TREATMENT OF CANCER

CROSS REFERENCE TO RELATED APPLICATIONS

Figure 1:
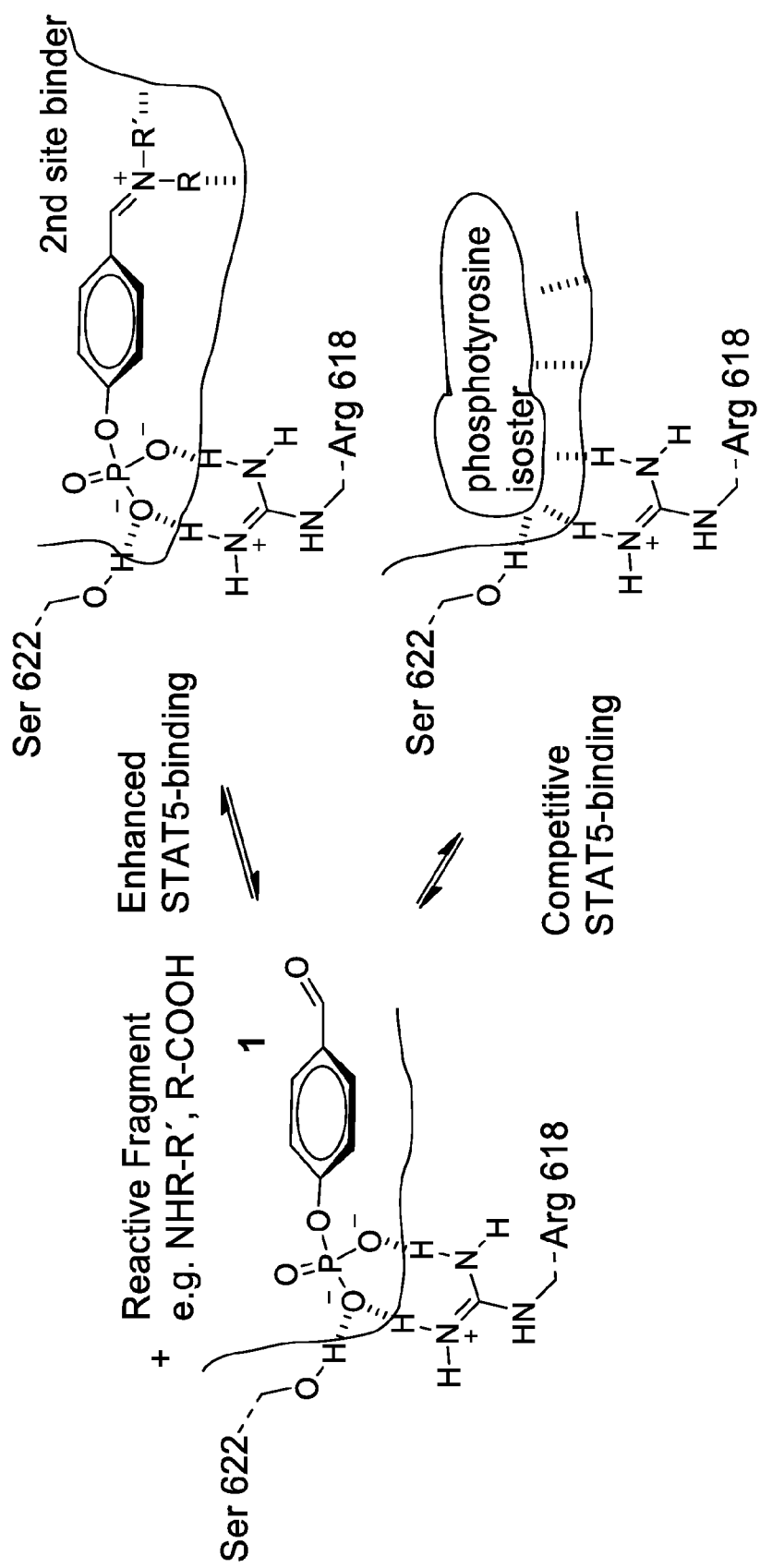

This U.S. Application is a National Phase Entry of PCT/EP2017/075394 filed on Oct. 5, 2017, entitled "NOVEL FURAZAN-3-CARBOXYLIC ACID DERIVATIVES AND USE THEREOF IN TREATMENT OF CANCER", which claims priority to European Application No. 16192394.1 filed on Oct. 5, 2016, the entireties of which are hereby incorporated herein by reference.

Acute myeloid leukemia (AML), also known as acute myelogenous leukemia, is a cancer of the myeloid line of blood cells, characterized by rapid growth of abnormal white blood cells that accumulate in the bone marrow and interfere with the production of normal blood cells. As an acute leukemia, AML progresses rapidly and is typically fatal within weeks or months if left untreated. AML is the most prevalent form of adult acute leukemia, particularly among older adults and is slightly more common in men than women. There is an estimated prevalence of 30,000 cases of AML in the US and 47,000 in the EU.

The incidence of AML increases with age with a median age at diagnosis of 67 years. The global incidence CAGR for AML out to 2013 is 1.4%. An aging population, along with an increased incidence of treatment-related AML in cancer survivors, currently accounting for 10-20% of all AML cases, is expected to drive the incidence of AML. In addition, there is some geographic variation in the incidence of AML. In adults, the highest rates are seen in North America, Europe, and Oceania, while adult AML is rarer in Asia and Latin America.

AML accounts for approximately 1.2% of all cancer deaths. The 5 year survival rates for AML are low, driven by therapy failure and patients relapsing. Among patients<65 the 5 year survival rate is 34.4%, among patients>65 it is only 5%.

The WHO classification of myeloid neoplasms and acute leukemia is the current standard for classification of AML and incorporates genetic abnormalities into diagnostic algorithms. This classification is done by examining the appearance of the malignant cells under light microscopy and by using cytogenetics and molecular genetics to characterize any underlying chromosomal abnormalities or genetic changes.

The most commonly used chemotherapeutic compounds for treatment of AML are anthracyclines, epipodophyllotoxins, methotrexate, thiopurines, cytarabine and alkylant agents such as cyclophosphamide. While all of these treatments are known to be toxic and to cause many side effects, there is still a need for new and efficient therapeutic concepts for the treatment of cancer diseases, like AML.

It is an object of the present invention to provide alternatives to known means for treatment of cancer, in particular of leukemia, like e.g. chronic and/or acute myeloid leukemia (AML).

The present invention relates to furazan-3-carboxylic acid derivatives or pharmaceutically acceptable salts thereof as defined below and in the claims.

It has been surprisingly found that the furazan-3-carboxylic acid derivatives of the present invention are capable of inhibiting transcription factor STAT5. STAT5 is a transcription factor known to be involved in signalling cascades relevant in cancer, e.g. in cancer diseases including leukemia, lymphoma and solid tumors. The furazan-3-carboxylic acid derivatives of the present invention are suitable for inhibiting signalling via the transcription factor STAT5, are selective for STAT5 and are effective in a cellular model of acute myeloid leukemia. Thus, the furazan-3-carboxylic acid derivatives appear to be suitable for treatment of cancer, in particular of leukemia like e.g. chronic and/or acute myeloid leukemia (AML).

The furazan-3-carboxylic acid derivatives of the present invention are compounds of Formula 1:

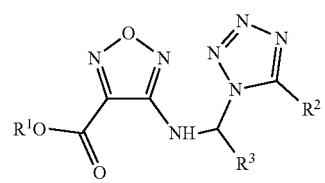

or a pharmaceutically acceptable salt thereof, wherein
$R^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and $[Q^1]_{m1}$-$L^1$;
$Q^1$ is a substituted or non-substituted bridging group selected from $C_1$-$C_{10}$-alkylene, $C_2$-$C_{10}$-alkenylene, $C_2$-$C_{10}$-alkynylene, —CH$_2$O—, —CH(CH$_3$)O—, —CH$_2$CH$_2$O—, —CH$_2$CH$_2$CH$_2$O—, —CH(CH$_3$)CH$_2$O—, and —CH$_2$CH(CH$_3$)O—;
m1 is an integer in the range of 1 to 10;
$L^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and —C(O)CH$_3$,
wherein in the above mentioned substituted groups one or more hydrogens are independently replaced by a substituent selected from deuterium, —F, —Cl, —Br, —I, and $C_1$-$C_6$-alkoxy;
$R^2$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and $[Q^2]_{m2}$-$Ar^1$-$[Q^3]_{m3}$-$[Ar^2]_{m4}$;
$Q^2$ is a substituted or non-substituted bridging group selected from $C_1$-$C_{10}$-alkylene, $C_2$-$C_{10}$-alkenylene, $C_2$-$C_{10}$-alkynylene, $C_6$-$C_{18}$-arylene, $C_5$-$C_{18}$-heteroarylene, —(C$_n$H$_{2n}$)O(C$_n$H$_{2n}$)—, —(C$_n$H$_{2n}$)NH(C$_n$H$_{2n}$)—, —(C$_n$H$_{2n}$)C(O)O(C$_n$H$_{2n}$)—, —(C$_n$H$_{2n}$)C(O)NH(C$_n$H$_{2n}$)—, and —(C$_n$H$_{2n}$)C(O)NHC(O)(C$_n$H$_{2n}$)—;
$Q^3$ is O or a substituted or non-substituted bridging group selected from $C_1$-$C_{10}$-alkylene, $C_2$-$C_{10}$-alkenylene, $C_2$-$C_{10}$-alkynylene, $C_6$-$C_{18}$-arylene, $C_5$-$C_{18}$-heteroarylene, —O(C$_n$H$_{2n}$)—, —(C$_n$H$_{2n}$)O(C$_n$H$_{2n}$)—, —(C$_n$H$_{2n}$)NH(C$_n$H$_{2n}$)—, —(C$_n$H$_{2n}$)C(O)O(C$_n$H$_{2n}$)—, —(C$_n$H$_{2n}$)C(O)NH(C$_n$H$_{2n}$)—, and —(C$_n$H$_{2n}$)C(O)NHC(O)(C$_n$H$_{2n}$)—;
$Ar^1$ and $Ar^2$ are independently from each other a $C_6$-$C_{18}$-aryl group or a substituted $C_6$-$C_{18}$-aryl group, wherein one or more hydrogens are independently replaced by a substituent selected from deuterium, —F, —Cl, —Br, —I, —C$_n$H$_{2n+1}$, —C$_n$F$_{2n+1}$, —O(C$_n$H$_{2n+1}$), —O(C$_n$F$_{2n+1}$), —OH, —NH$_2$, —NH(C$_n$H$_{2n+1}$), —N(C$_n$H$_{2n+1}$)$_2$, —NHS(O)$_2$C$_n$H$_{2n-1}$, and —N(C$_n$H$_{2n+1}$)S(O)$_2$C$_n$H$_{2n-1}$;
m2 and m3 are independently from each other an integer in the range of 0 to 5;

m4 is 0 or 1;

n is an integer in the range of 1 to 5; and $R^3$ is hydrogen or substituted or non-substituted $C_1$-$C_{10}$-alkyl, with the proviso that $R^1$, $R^2$, and $R^3$ cannot simultaneously all be hydrogen.

As used in this specification and appended claims, the singular forms "a", "an" and "the" include singular and plural referents unless the content clearly dictates otherwise.

In Formula 1, $R^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and $[Q^1]_{m1}$-$L^1$;

wherein $Q^1$ is a substituted or non-substituted bridging group selected from $C_1$-$C_{10}$-alkylene, $C_2$-$C_{10}$-alkenylene, $C_2$-$C_{10}$-alkynylene, —$CH_2O$—, —$CH(CH_3)O$—, —$CH_2CH_2O$—, —$CH_2CH_2CH_2O$—, —$CH(CH_3)CH_2O$—, and —$CH_2CH(CH_3)O$—;

m1 is an integer in the range of 1 to 10;

$L^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and —$C(O)CH_3$, and wherein in the above mentioned substituted groups one or more hydrogens are independently replaced by a substituent selected from deuterium, —F, —Cl, —Br, —I, and $C_1$-$C_6$-alkoxy.

In Formula 1, $R^1$ is preferably selected from hydrogen or a substituted or non-substituted group selected from $C_1$-$C_4$-alkyl, $C_2$-$C_4$-alkenyl, $C_2$-$C_4$-alkynyl, $C_6$-$C_{12}$-aryl, $C_5$-$C_{12}$-heteroaryl, and $[Q^1]_{m1}$-$L^1$;

wherein $Q^1$ is a substituted or non-substituted bridging group selected from $C_1$-$C_4$-alkylene, $C_2$-$C_4$-alkenylene, $C_2$-$C_4$-alkynylene, —$CH_2O$—, —$CH(CH_3)O$—, —$CH_2CH_2O$—, —$CH_2CH_2CH_2O$—, —$CH(CH_3)CH_2O$—, and —$CH_2CH(CH_3)O$—; m1 is an integer in the range of 1 to 10; $L^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and —$C(O)CH_3$, wherein in the above mentioned substituted groups one or more hydrogens are independently replaced by a substituent selected from deuterium, —F, —Cl, —Br, —I, and $C_1$-$C_6$-alkoxy.

Particularly preferred groups for $R^1$ comprise hydrogen, methyl, n-butyl or —$CH(CH_3)OC(O)CH_3$.

In Formula 1, $R^2$ represents hydrogen or a substituted or non-substituted group selected from $C_6$-$C_{18}$-aryl, and $[Q^2]_{m2}$-$Ar^1$-$[Q^3]_{m3}$-$[Ar^2]_{m4}$;

wherein $Q^2$ is a substituted or non-substituted bridging group selected from $C_1$-$C_4$-alkylene and —$(C_nH_{2n})NH(C_nH_{2n})$—;

$Q^3$ is O or —$O(C_nH_{2n})$—;

$Ar^1$ and $Ar^2$ are independently selected from a $C_6$-$C_{18}$-aryl group or a substituted $C_6$-$C_{18}$-aryl group, wherein one or more hydrogens are independently replaced by a substituent selected from —F, —Cl, —$C_nH_{2n+1}$, —$C_nF_{2n+1}$, —$O(C_nH_{2n+1})$, —$O(C_nF_{2n+1})$, —OH, and —$NHS(O)_2C_nH_{2n-1}$;

m2, m3, and m4 are independently from each other 0 or 1; and n is an integer in the range of 1 to 4.

In Formula 1, $R^2$ is preferably selected from hydrogen or a substituted or non-substituted group selected from $C_6$-$C_{10}$-aryl, and $[Q^2]_{m2}$-$Ar^1$-$[Q^3]_{m3}$-$[Ar^2]_{m4}$;

wherein $Q^2$ is a substituted or non-substituted bridging group selected from $C_1$-$C_4$-alkylene and —$(C_nH_{2n})NH(C_nH_{2n})$—;

$Q^3$ is O or —$O(C_nH_{2n})$;

$Ar^1$ and $Ar^2$ are independently selected from a $C_6$-$C_{10}$-aryl group or a substituted $C_6$-$C_{10}$-aryl group, wherein one or more hydrogens are independently replaced by a substituent selected from —F, —Cl, —$C_nH_{2n+1}$, —$C_nF_{2n+1}$, —$O(C_nH_{2n+1})$, —$O(C_nF_{2n+1})$, —OH, and —$NHS(O)_2C_nH_{2n-1}$;

m2, m3, and m4 are independently from each other 0 or 1; and n is an integer in the range of 1 to 4.

Alternatively, in Formula 1 $R^2$ represents hydrogen or a substituted or non-substituted group selected from $C_6$-aryl, and $[Q^2]_{m2}$-$Ar^1$-$[Q^3]_{m3}$-$[Ar^2]_{m4}$;

wherein $Q^2$ is a substituted or non-substituted bridging group selected from $C_1$-$C_4$-alkylene and —$(C_nH_{2n})NH(C_nH_{2n})$—;

$Q^3$ is O or —$O(C_nH_{2n})$;

$Ar^1$ and $Ar^2$ are independently selected from a $C_6$-aryl group or a substituted $C_6$-aryl group, wherein one or more hydrogens are independently replaced by a substituent selected from —F, —Cl, —$C_nH_{2n+1}$, —$C_nH_{2n+1}$, —$O(C_nH_{2n+1})$, —$O(C_nH_{2n+1})$, —OH, and —$NHS(O)_2C_nH_{2n-1}$;

m2, m3, and m4 are independently from each other 0 or 1; and n is an integer in the range of 1 to 4.

Particularly preferred groups for $R^2$ comprise hydrogen, phenyl or one of Formulae 2-1 to 2-22:

2-1

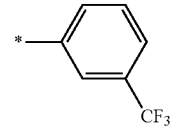

2-2

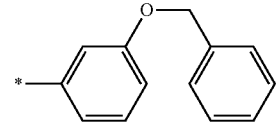

2-3

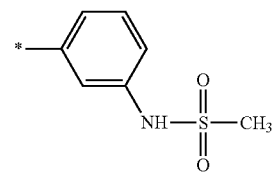

2-4

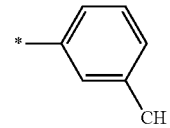

2-5

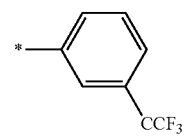

2-6

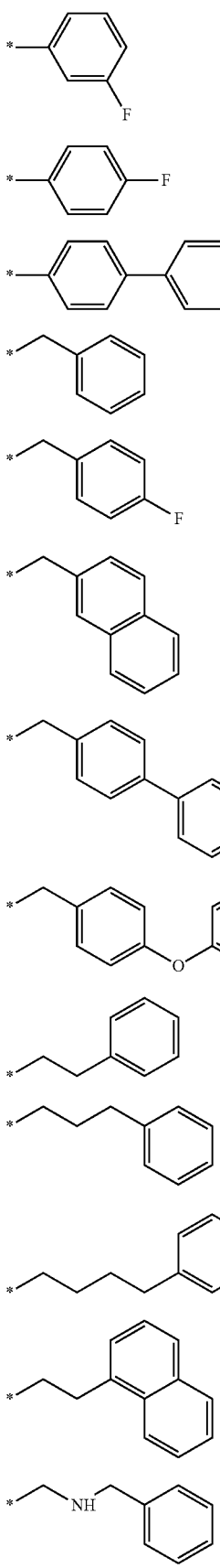

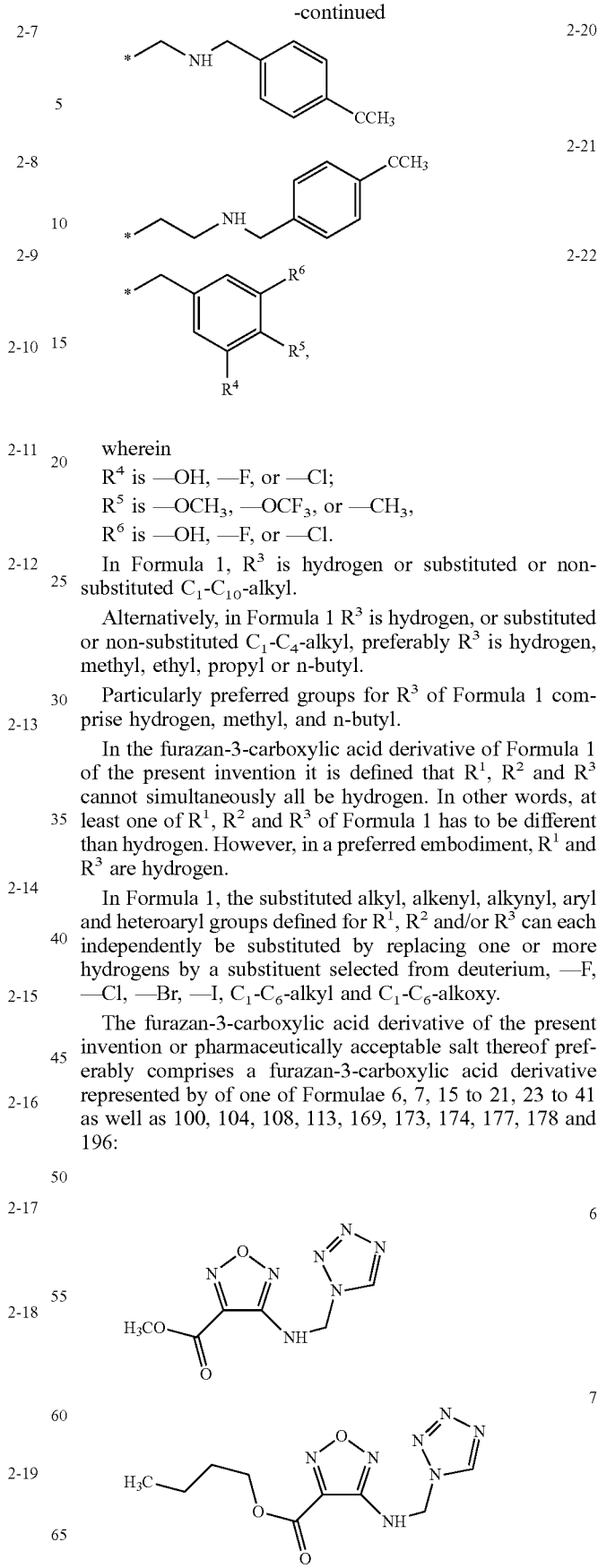

wherein
R⁴ is —OH, —F, or —Cl;
R⁵ is —OCH₃, —OCF₃, or —CH₃,
R⁶ is —OH, —F, or —Cl.

In Formula 1, $R^3$ is hydrogen or substituted or non-substituted $C_1$-$C_{10}$-alkyl.

Alternatively, in Formula 1 $R^3$ is hydrogen, or substituted or non-substituted $C_1$-$C_4$-alkyl, preferably $R^3$ is hydrogen, methyl, ethyl, propyl or n-butyl.

Particularly preferred groups for $R^3$ of Formula 1 comprise hydrogen, methyl, and n-butyl.

In the furazan-3-carboxylic acid derivative of Formula 1 of the present invention it is defined that $R^1$, $R^2$ and $R^3$ cannot simultaneously all be hydrogen. In other words, at least one of $R^1$, $R^2$ and $R^3$ of Formula 1 has to be different than hydrogen. However, in a preferred embodiment, $R^1$ and $R^3$ are hydrogen.

In Formula 1, the substituted alkyl, alkenyl, alkynyl, aryl and heteroaryl groups defined for $R^1$, $R^2$ and/or $R^3$ can each independently be substituted by replacing one or more hydrogens by a substituent selected from deuterium, —F, —Cl, —Br, —I, $C_1$-$C_6$-alkyl and $C_1$-$C_6$-alkoxy.

The furazan-3-carboxylic acid derivative of the present invention or pharmaceutically acceptable salt thereof preferably comprises a furazan-3-carboxylic acid derivative represented by of one of Formulae 6, 7, 15 to 21, 23 to 41 as well as 100, 104, 108, 113, 169, 173, 174, 177, 178 and 196:

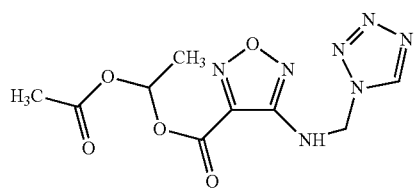
15
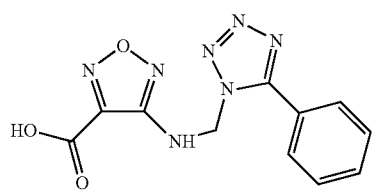
16
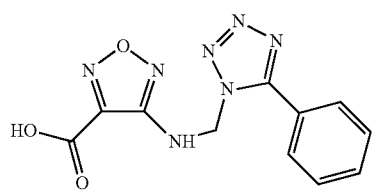
17
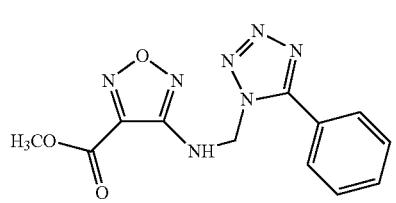
18
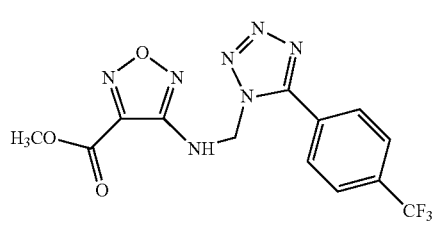
19
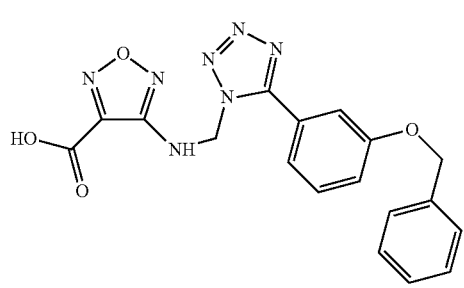
20
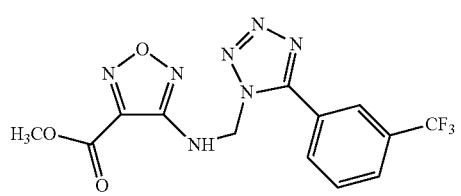
21
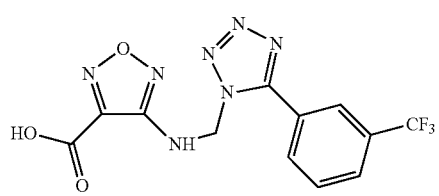
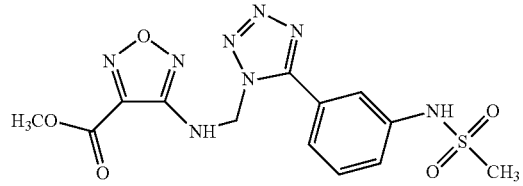
23
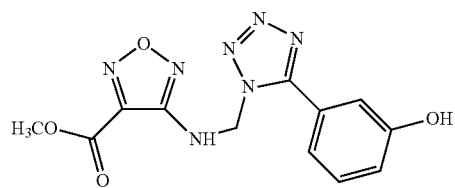
24
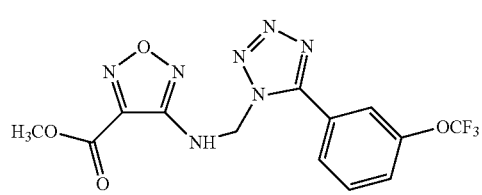
25
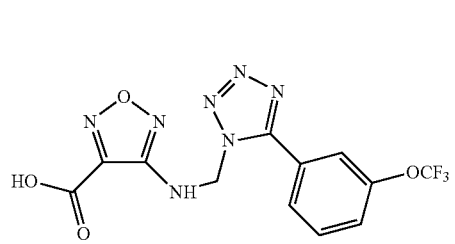
26
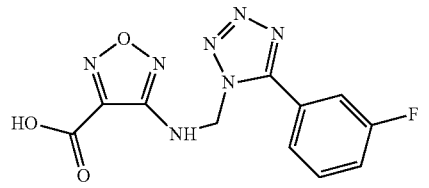
27
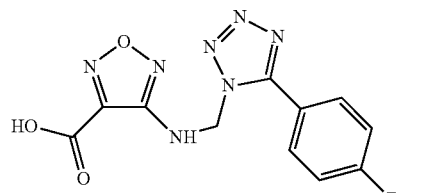
28
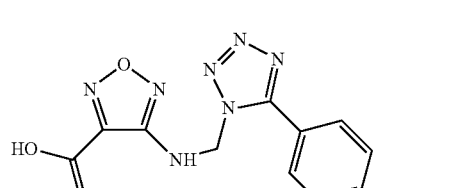
29

30
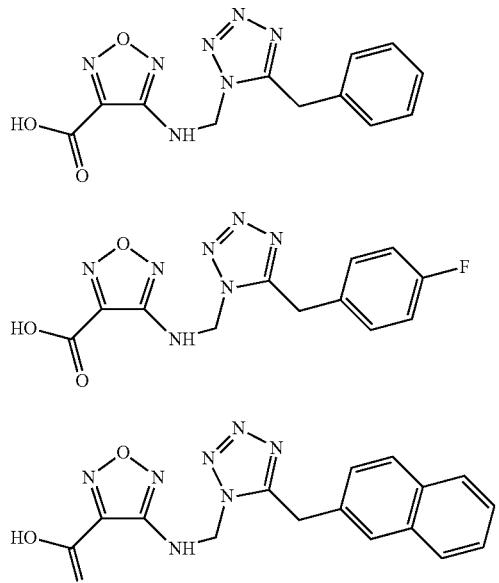
31
32
33
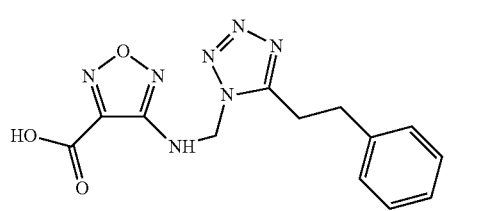
34
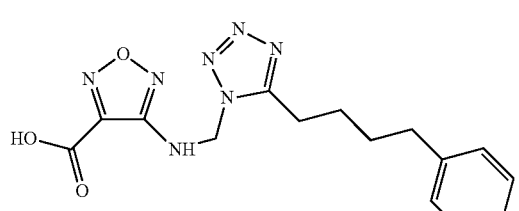
35
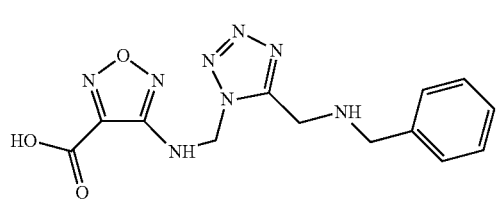
36
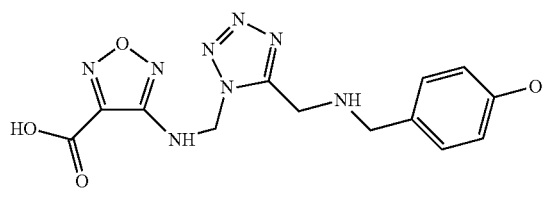
37
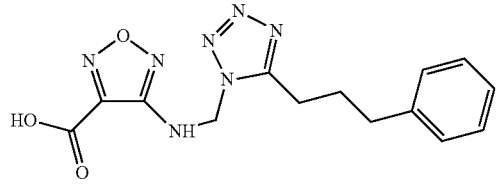
38
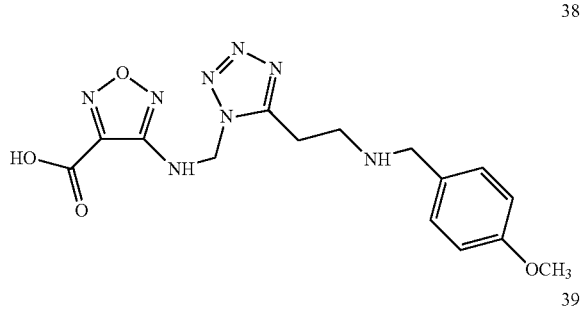
39
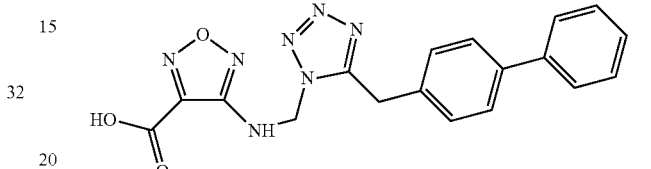
40
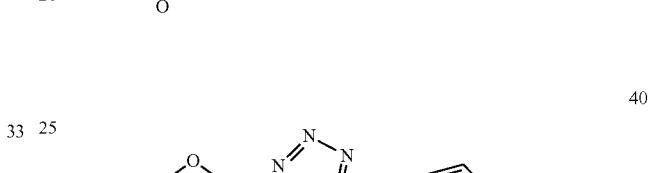
41
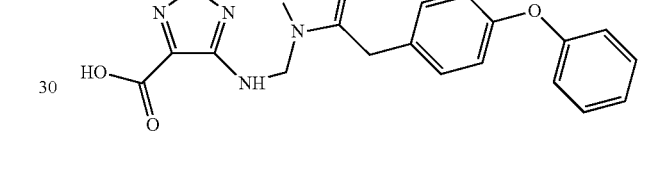
100
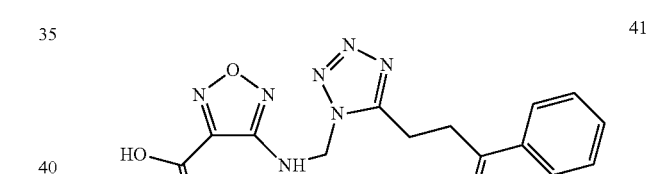
104
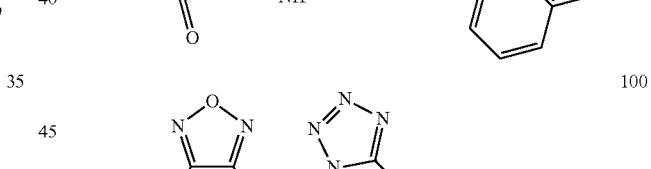
108
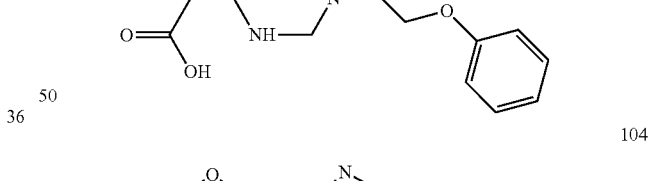

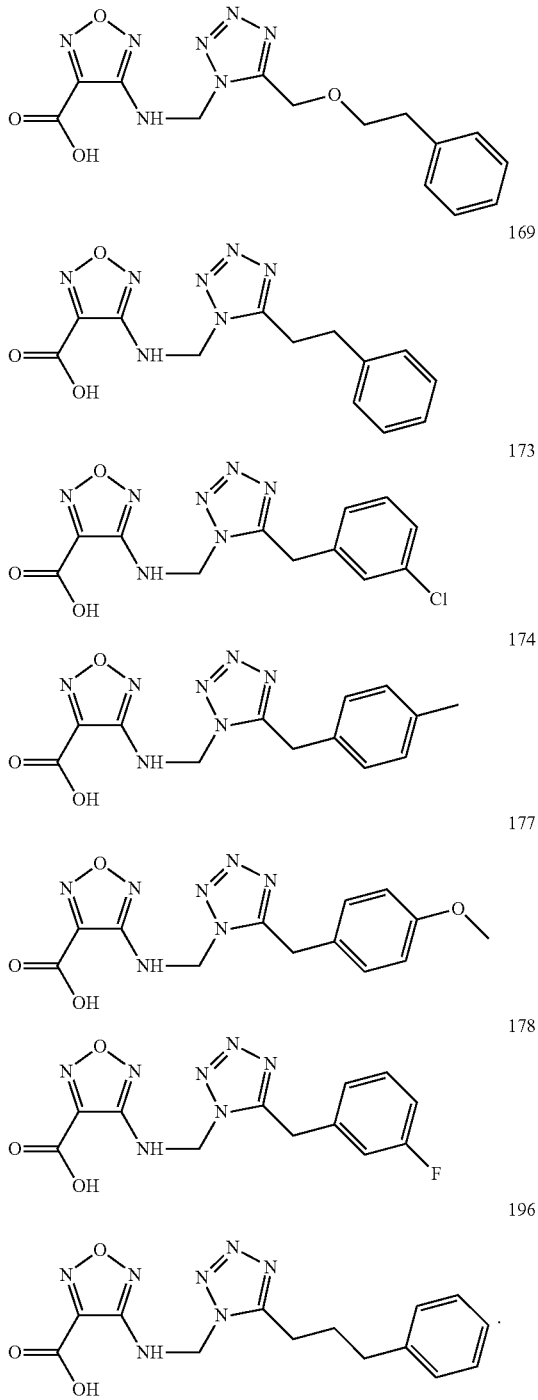

The furazan-3-carboxylic acid derivatives of the present invention may be in the form of a pharmaceutically acceptable salt. As used herein, the term "pharmaceutically acceptable salt" includes acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). When the compounds of the present invention possess a free base form, the compounds can be prepared as a pharmaceutically acceptable acid addition salt by reacting the free base form of the compound with a pharmaceutically acceptable inorganic or organic acid, e.g. hydrohalides such as hydrochloride, hydrobromide, hydroiodide; other mineral acids and their corresponding salts such as sulfate, nitrate, phosphate, etc.; and alkyl- and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include adipate, alginate, arginate, aspartate, benxenesulfonate (hesylate), bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, ethanesulfonate, fumarate, galacterate (from mucic acid), galacturonate, glucoheptaoate, glucorrate, glutamate, glycerophosplrate, hemisueci-nate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include copper, ferric, ferrous, lithium, magnesium, manganic, manganous, potassium, sodium and zinc salts. Organic base salts include salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, diethylamine, 2-diethylaminoethanol, Z-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamirre, trimethylamine, tripropylamine and tris-(hydroxymethyl)-methylamine (tromethamine).

Salts of the furazan-3-carboxylic acid derivatives of the present invention may also be prepared by exchanging a counter-ion of a compound of the invention in the form of a salt with another counter-ion, for example using a suitable ion exchange resin. The salt form may confer improved pharmacokinetic properties on the furazan-3-carboxylic acid derivatives as compared to the free form of the compound. The pharmaceutically acceptable salt form may also positively affect the pharmacodynamics of the compound with respect to its therapeutic activity in the body. An example of pharmacodynamics property that may be favorably affected is the manner in which the compound is transported across cell membranes, which in turn may directly and positively affect the adsorption, distribution, biotransformation and excretion of the compound.

In a particular preferred embodiment of the furazan-3-carboxylic acid derivatives of the present invention, the pharmaceutically acceptable salts thereof comprise inorganic acid salts such as chlorides, hydrochlorides, sulfates, bisulfates, nitrates, hydrobromides, hydroiodides and phosphates; organic carboxylates such as acetates, lactates, citrates, oxalates, glutarates, malates, tartrates, bitartrates, fumarates, mandelates, maleates, succinates, benzoates and phthalates; organic sulfonates such as methanesulfonates, ethansulfonates, benzenesulfonates, p-toluenesulfonates and camphor-sulfonates.

According to a further aspect of the present invention, the furazan-3-carboxylic acid derivatives of the present invention are suitable as a medicament, e.g. for use in the treatment of diseases.

As used herein, the term "treating" encompasses to reversing, alleviating or inhibiting the progress of a disease, disorder or condition, or improvement of one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein the term "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

Examples of various diseases that may be treated using the furazan-3-carboxylic acid derivatives of the present invention can be diseases involving undesirable or uncontrolled cell proliferation. Such indications include cancer, e.g. benign tumors, various types of cancers such as primary tumors and tumor metastasis. The furazan-3-carboxylic acid derivatives of the present invention are particularly useful in treatment of cancer that is associated with increased STAT5 signaling compared to corresponding non-tumorous tissue, with constitutively active STAT5 signaling and/or cancer that is sensitive to inhibition of STAT5 signaling activity. Tests to measure STAT5 signaling activity are well known in the art and exemplary embodiments of such tests are described in the experimental section of this specification. More specific indications are cancers associated with abnormal proliferation of white blood cells, e.g. leukemia. In particular, the furazan-3-carboxylic acid derivatives of the present invention are useful in treatment of chronic and/or acute myeloid leukemia (CML, classified in ECD-10 as C92.1; AML, classified in ICD-10 as C92.0).

The present invention is in particular directed to the furazan-3-carboxylic acid derivatives of the present invention for use in the treatment of cancer, preferably of leukemia, more preferably of chronic and/or acute myeloid leukemia.

The present invention also relates to the use of the furazan-3-carboxylic acid derivatives of the present invention for the manufacture of a medicament for the treatment of cancer, preferably leukemia, more preferably chronic and/or acute myeloid leukemia.

The present invention also relates to a method for treating cancer, wherein a patient in need of such therapy is administered a therapeutically effective dose of a furazan-3-carboxylic acid derivative of the present invention or a pharmaceutically acceptable salt thereof. Preferably, the cancer is selected from leukemia, more preferably the cancer is chronic and/or acute myeloid leukemia.

Further, the present invention is also directed to the furazan-3-carboxylic acid derivative of Formula 3:

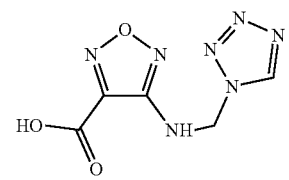

3 or pharmaceutically acceptable salt thereof for use in treatment of cancer, preferably leukemia, more preferably chronic and/or acute myeloid leukemia. The furazan-3-carboxylic acid derivative of Formula 3 represents a furazan-3-carboxylic acid derivative according to Formula 1, with the proviso that $R^1$, $R^2$ and $R^3$ all are hydrogen.

The present invention also relates to a pharmaceutical composition comprising as an active ingredient a furazan-3-carboxylic acid derivative of the present invention. Such pharmaceutical compositions may comprise, in addition to the furazan-3-carboxylic acid derivative of the invention or its pharmaceutically acceptable salt, one or more pharmaceutically acceptable excipients. The term "excipient" is used herein to describe any ingredient other than the furazan-3-carboxylic acid derivative of the invention. The choice of excipient will to a large extent depend on the particular mode of administration. Excipients can e.g. be suitable carriers, retardants, boosters, prolonging substances, adjuvants, stabilizers, binders, emulsifiers, surface active agents, penetration enhancers suspending agents, disintegrants, buffers, salts, dilutents, solvents, dispersion media, fillers, lubricants, propellants, preservatives, flavours or mixtures thereof.

Another aspect of the present invention relates to a a pharmaceutical combination comprising at least one furazan-3-carboxylic acid derivative of the invention or pharmaceutically acceptable salt thereof as active ingredient together with at least one pharmaceutically acceptable carrier, excipient and/or diluent.

Optionally, said pharmaceutical composition further comprises at least one anticancer agent selected from a group consisting of a JAK inhibitor, a BCR-ABL inhibitor, a FLT3 inhibitor, and a PI3K inhibitor. As used herein the term "pharmaceutical combination" refers to a combination of at least to pharmaceutically active agents or therapeutic agents with or without further ingredients, carrier, diluents and/or solvents. As used herein the term "pharmaceutical composition" refers to a galenic formulation of at least one pharmaceutically active agent together with at least one further ingredient, carrier, diluent and/or solvent.

Compounds of formula 1 may be administered as the sole pharmaceutical agent or in combination with at least one anticancer agent selected from a group consisting of a JAK inhibitor, a BCR-ABL inhibitor, a FLT3 inhibitor, and a PI3K inhibitor, wherein the pharmaceutical combination causes no unacceptable adverse effects. This combination therapy includes administration of a single pharmaceutical dosage formulation, which contains a compound of formula 1 and one or more additional anticancer agents in form of a single pharmaceutical composition, as well as administration of the compound of formula 1 and each additional anticancer agent in its own separate pharmaceutical dosage formulation, i.e. in its own separate pharmaceutical composition. For example, a compound of formula 1 and an anticancer agent may be administered to the patient together in a single oral dosage composition such as a tablet or capsule, or each agent may be administered in separate pharmaceutical compositions.

Where separate pharmaceutical compositions are used, the compound of formula 1 and one or more additional anticancer agents may be administered at essentially the same time (e.g., concurrently) or at separately staggered times (e.g., sequentially).

"Pharmaceutical combination" as used herein means a product that results from the mixing or combining of more than one active ingredient and includes both fixed and non-fixed combinations of the active ingredients.

The term "fixed combination" or "fixed dose" means that the active ingredients, e.g. a compound of formula 1 and a combination partner, i.e. an anticancer agent, are both administered to a patient simultaneously in the form of a single entity or dosage. In other terms: the active ingredients are present in one dosage form, e.g. in one tablet or in one capsule.

The term "non-fixed combination" means that the active ingredients, e.g. a compound of formula 1 and a combination partner, i.e. an anticancer agent, are both administered to a patient as separate entities either simultaneously, concurrently or sequentially with no specific time limits, wherein such administration provides therapeutically effective levels of the two compounds in the body of a mammal or human in need thereof. The latter also applies to cocktail therapy, e.g. the administration of three or more anticancer agents.

Said anticancer agent is as kinase inhibitor selected from a group consisting of a JAK inhibitor, a BCR-ABL inhibitor, a FLT3 inhibitor, and a PI3K inhibitor.

Said pharmaceutical combination may be administered independently at the same time or separately within time intervals, especially here these time intervals allow that the combination partners show a synergistic effect.

The term "synergistic effect" means a therapeutic effect observed following administration of two or more active ingredients (e.g., at least one compound of the invention as STAT5b inhibitor and one or more kinase inhibitors as anticancer agents selected from a group consisting of a JAK inhibitor, a BCR-ABL inhibitor, a FLT3 inhibitor, and a PI3K inhibitor) that is greater than the sum of the therapeutic effects observed following the administration of each single agent.

By "synergistic increase" is meant the combination of two or more active ingredients (e.g., at least one compound of the invention as STAT5b inhibitor and one or more anticancer agents selected from a group consisting of a JAK inhibitor, a BCR-ABL inhibitor, a FLT3 inhibitor, and a PI3K inhibitor) that results in an increase in cancer cell death that is greater than the sum of the cancer cell death observed following the administration of each individual agent.

By "synergistic decrease" is meant the combination of two or more active ingredients (e.g., at least one compound of the invention as STAT5b inhibitor and one or more anticancer agents selected from the group consisting of a JAK inhibitor, a BCR-ABL inhibitor, a FLT3 inhibitor, and a PI3K inhibitor) that results in a decrease in one or more symptoms of a cancer that is greater than the sum of the decrease in one or more symptoms of the cancer observed following the administration of each individual agent.

In another example of synergy, a therapeutic effect is observed for the combination of two or more active ingredients, wherein one or more of the active ingredients are present at a dose that is normally non-therapeutic. In another example of synergy, the combination of two or more active ingredients results in an unexpected decrease in toxicity (i.e., a level of toxicity that is less than the sum of the toxicity observed following administration of the single agents).

The term "STAT5b inhibitor" means any active ingredient that binds STAT5b and inhibits a biological activity (e.g., kinase activity) of STAT5b or inhibits dimerization of two STAT5bs.

The term "inhibits" and its grammatical conjugations, such as "inhibitory", is not intended to require complete inhibition in Stat5b activity. Such reduction is preferably by at least about 50%, at least about 75%, at least about 90%, and more preferably by at least about 95% of the activity of the molecule in the absence of the inhibitory effect, e.g., in the absence of an inhibitor. Most preferably, the term refers to an observable or measurable reduction in activity.

In treatment scenarios, preferably the inhibition is sufficient to produce a therapeutic and/or prophylactic benefit in the condition being treated. The phrase "does not inhibit" and its grammatical conjugations do not require a complete lack of effect on the activity. For example, it refers to situations where there is less than about 20%, less than about 10%, and preferably less than about 5% of reduction in kinase activity in the presence of an inhibitor such as a compound of the invention.

"JAK (Janus Kinase) inhibitor" means any active ingredient that binds Janus kinase and inhibits a biological activity (e.g., kinase activity) thereof. Preferred, said JAK inhibitor is selected from a group consisting of Ruxolitinib, Tofacitinib, Baricitinib, Filgotinib, Lestaurtinib, Momelotinib, Pacritinib, Upadacitinib, Cucurbitacin I and CHZ868.

"BCR-ABL inhibitor" means any active ingredient that binds BCR-ABL tyrosine kinase and inhibits a biological activity (e.g., kinase activity) thereof. Preferred, said BCR-ABL inhibitor is selected from a group consisting of Imatinib, Nilotiniib, Dasatinib, Bosutinib, Ponatinib, and Bafetinib.

"FLT3 (FMS-like tyrosine kinase 3) inhibitor" means any active ingredient that binds FLT3 and inhibits a biological activity (e.g., kinase activity) thereof. Preferred, said FLT3 inhibitor is selected from a group consisting of Lestaurtinib, Midostaurin, Sorafenib, Quizartinib, and Crenolanib.

"PI3K (phosphoinositide 3-kinase) inhibitor" means any active ingredient that binds PI3K and inhibits a biological activity (e.g., kinase activity) thereof. Preferred, said PI3K inhibitor is selected from a group consisting of Idelalisib, Wortmannin, demethoxyviridin, Perifosine, Buparlisib, Duvelisib, Alpelisib, TGR 1202, Copanlisib, Dacotolisib, and PX-866.

It was found that said pharmaceutical combination has a synergistic effect for use in the treatment of cancer, preferably of leukemia, more preferably of chronic and/or acute myeloid leukemia.

The present invention is also directed to a method for treating cancer, wherein a patient in need of such therapy is administered a therapeutically effective dose of a pharmaceutical composition of the present invention. Preferably, the cancer is selected from leukemia, more preferably the cancer is acute myeloid leukemia.

The furazan-3-carboxylic acid derivatives of the invention are administered preferably at an effective dose. An "effective dose" is the dose of a furazan-3-carboxylic acid derivative that upon administration to a patient yields a measurable therapeutic effect with regard to the disease of interest. In the present invention an effective dose is the dose of a furazan-3-carboxylic acid derivative that upon administration to a patient yields a therapeutic effect with regard to at least one disease related symptom in a patient or patients suffering from said disease. Preferably, the furazan-3-carboxylic acid derivative of the invention is administered at a dose of not more than 500 mg/kg/d. In particular, the furazan-3-carboxylic acid derivative can be administered at a dose of 1 mg/kg/d to 400 mg/kg/d, preferably of 20 mg/kg/d to 150 mg/kg/d. In any event, the physician or the skilled person will be able to determine the actual dose which will be suitable for an individual patient, which is likely to vary with the age, weight, sex, and concomitant illnesses such as renal or hepatic dysfunction and response of the particular patient to be treated. The above mentioned dosages are exemplary of the average case. There can, of course, be individual instances where higher or lower dosage ranges are appropriate, and such are within the scope of the invention.

The furazan-3-carboxylic acid derivatives of the present invention are preferably administered orally, intravenously, subcutaneously, bucally, rectally, dermally, nasally, tracheally, bronchially or by any other parenteral route or via inhalation in a pharmaceutically acceptable dosage form.

The furazan-3-carboxylic acid derivatives of the present invention may be administered orally. Oral administration may involve swallowing, so that the compound enters the gastrointestinal tract, or buccal or sublingual administration may be employed by which the compound enters the blood stream directly from the mouth.

Formulations suitable for oral administration include: solid formulations such as tablets; capsules containing particulates, liquids, or powders; lozenges (including liquid-filled); and chews; multi- and nano-particulates; gels; solid solutions; liposomes; films, ovules, sprays and liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the compound may make up from 1 weight % to 80 weight % of the dosage form, more typically from 5 weight % to 60 weight % of the dosage form. In addition to the compound, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% compound, from about 10 weight % to about 90 weight % binder, from about 0 weight % to about 85 weight % diluent, from about 2 weight % to about 10 weight % disintegrant, and from about 0.25 weight % to about 10 weight % lubricant.

The furazan-3-carboxylic acid derivatives of the present invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art.

The furazan-3-carboxylic acid derivatives of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol.

The furazan-3-carboxylic acid derivatives of the present invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. The pressurised container, pump, spray, atomizer, or nebuliser contains a solution or suspension of the furazan-3-carboxylic acid derivatives of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

The use of furazan-3-carboxylic acid derivatives in the treatment of diseases, preferably of cancer, can have the advantage that such compounds may be more efficacious than, be less toxic than, be longer acting than, be more potent than, produce fewer side effects than, be more easily absorbable than, have better pharmacokinetic profile (e.g. higher oral bioavailability and/or lower clearance) than, and/or have other useful pharmacological, physical, or chemical properties over compounds known in the prior art for treatment of said diseases.

FIGURES

FIG. 1. Fragment ligation assay for detecting nucleophilic fragments, which can either enhance the binding of 4-formyl-phenyl phosphate 1, or replace 1 competitively.

Figure 2:
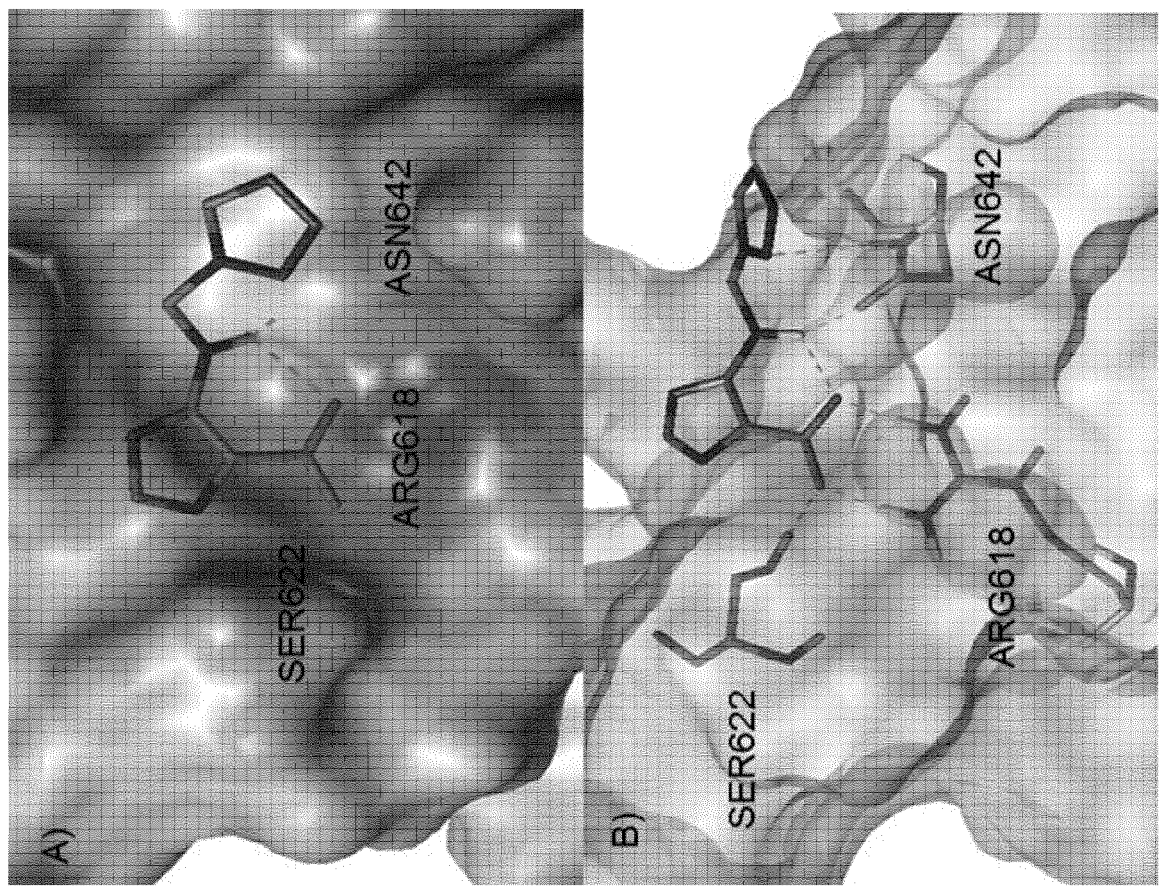

FIG. 2. Molecular docking results of compound 3 into a homology model of human STAT5b-SH2 domain, generated from the published structure of STAT5a (PDB accession codes, 1Y1U). (A) Predicted binding mode of 3. on protein surface (pink=negatively charged residues; blue=positively charged residues); (B) Hydrogen bonds of 3 with key residues in the hydrophilic binding pocket of the SH2 domain, ligand and key interacting protein residues are shown as sticks.

Figure 3:
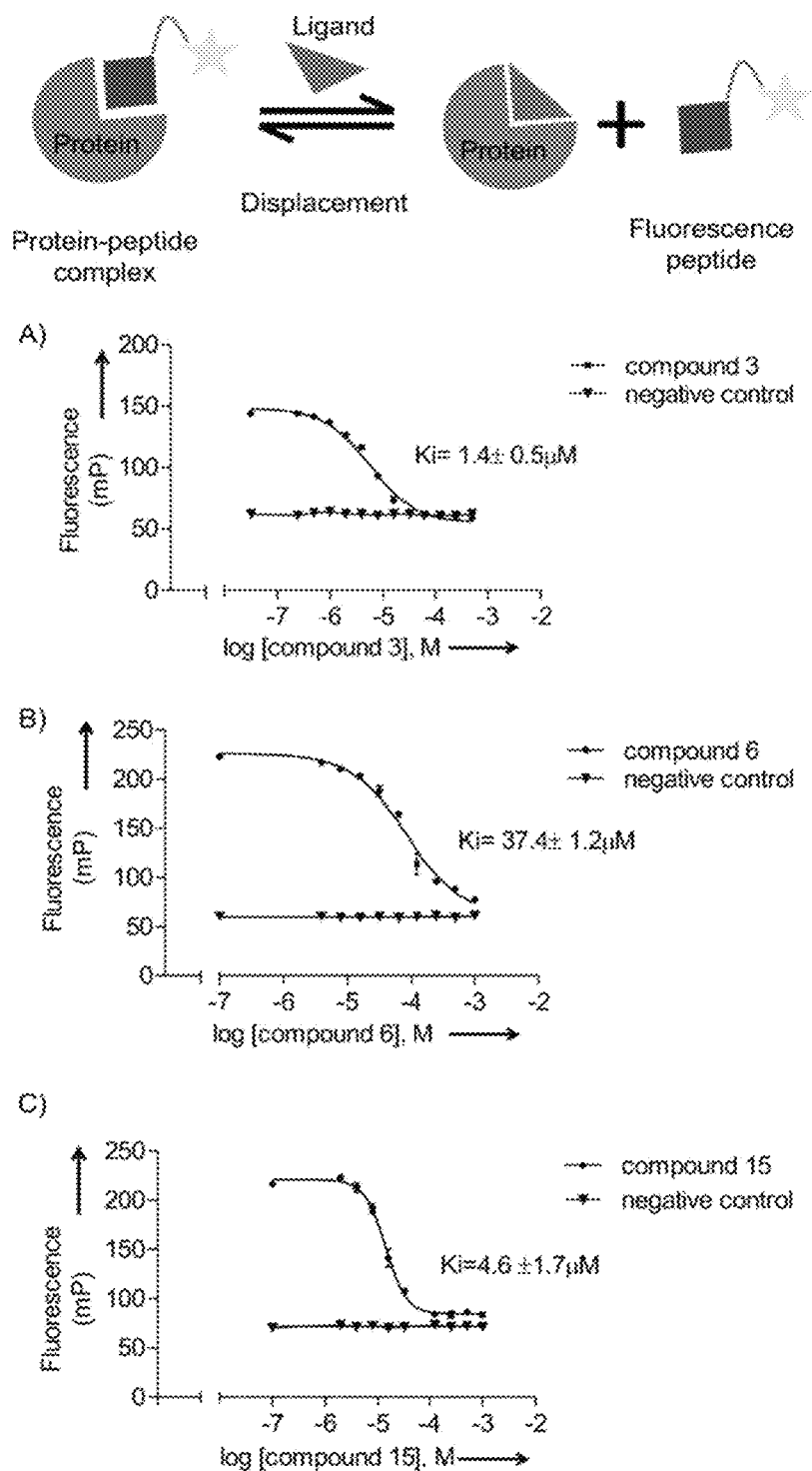

FIG. 3. Fluorescence polarization curve for the binding of compound 3 (A), 6 (B) and 15 (C) to recombinant STAT5-SH2 domain.

Figure 4:
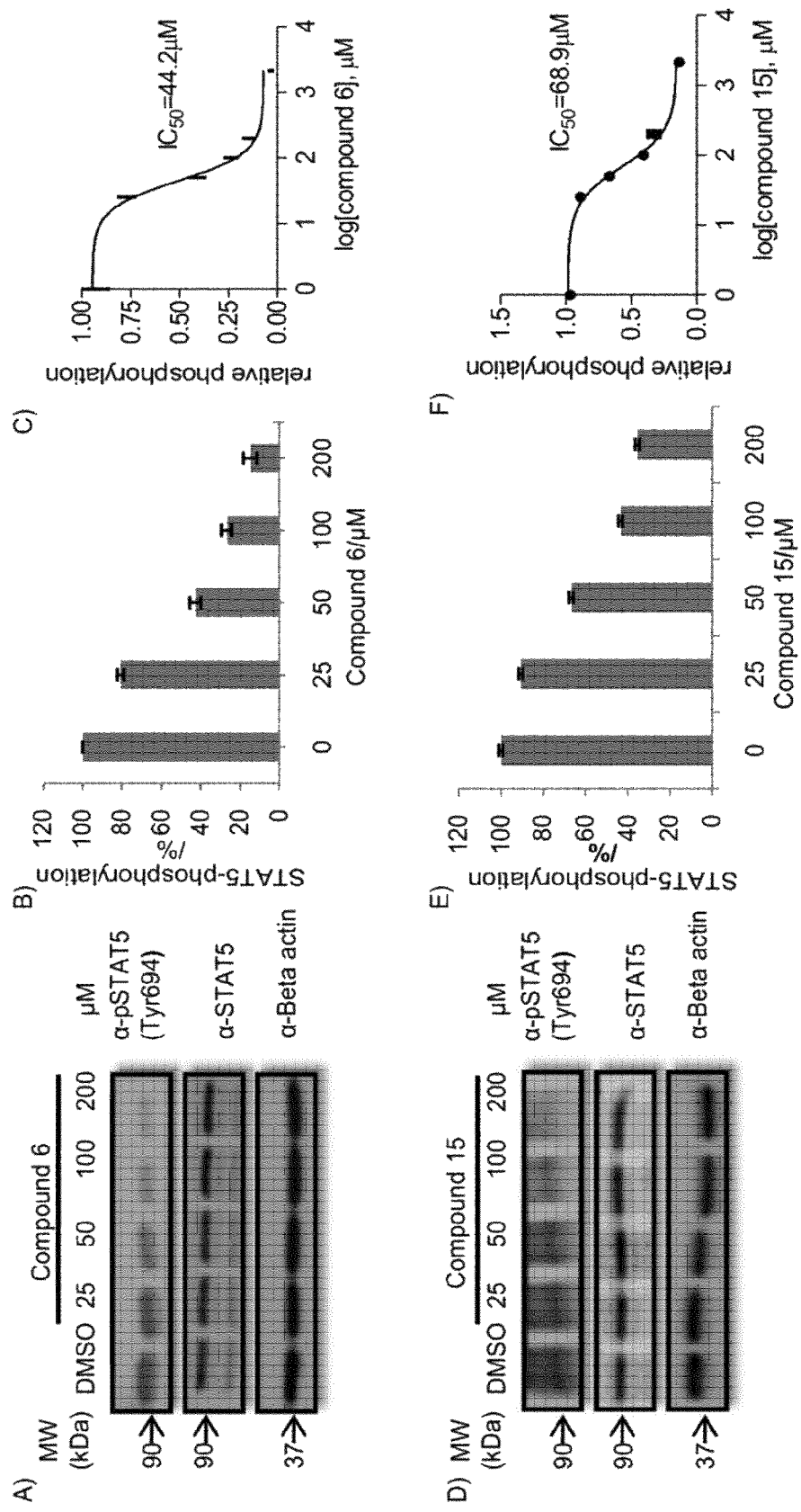

FIG. 4. Compounds 6 and 15 and decrease the tyrosine phosphorylation of STAT5 in a dose dependent manner leading to inhibition of cell proliferation in BaF3/FLT3-ITD cells. Western blot analysis of STAT5 inhibition in BaF3/FLT3-ITD cells after 6 h treatment with compound 6 (A) and 15 (D). Relative STAT5 phosphorylation levels were plotted as in (B and E) and $IC_{50}$ values of phosphorylated STAT5 inhibition (C and F) were calculated using GraphPad Prism 5 software after quantification using Image J software. Experiments were repeated twice; errors bars represent SD. Immunoblotting for beta-actin was used as a control for uniform protein loading.

Figure 5:
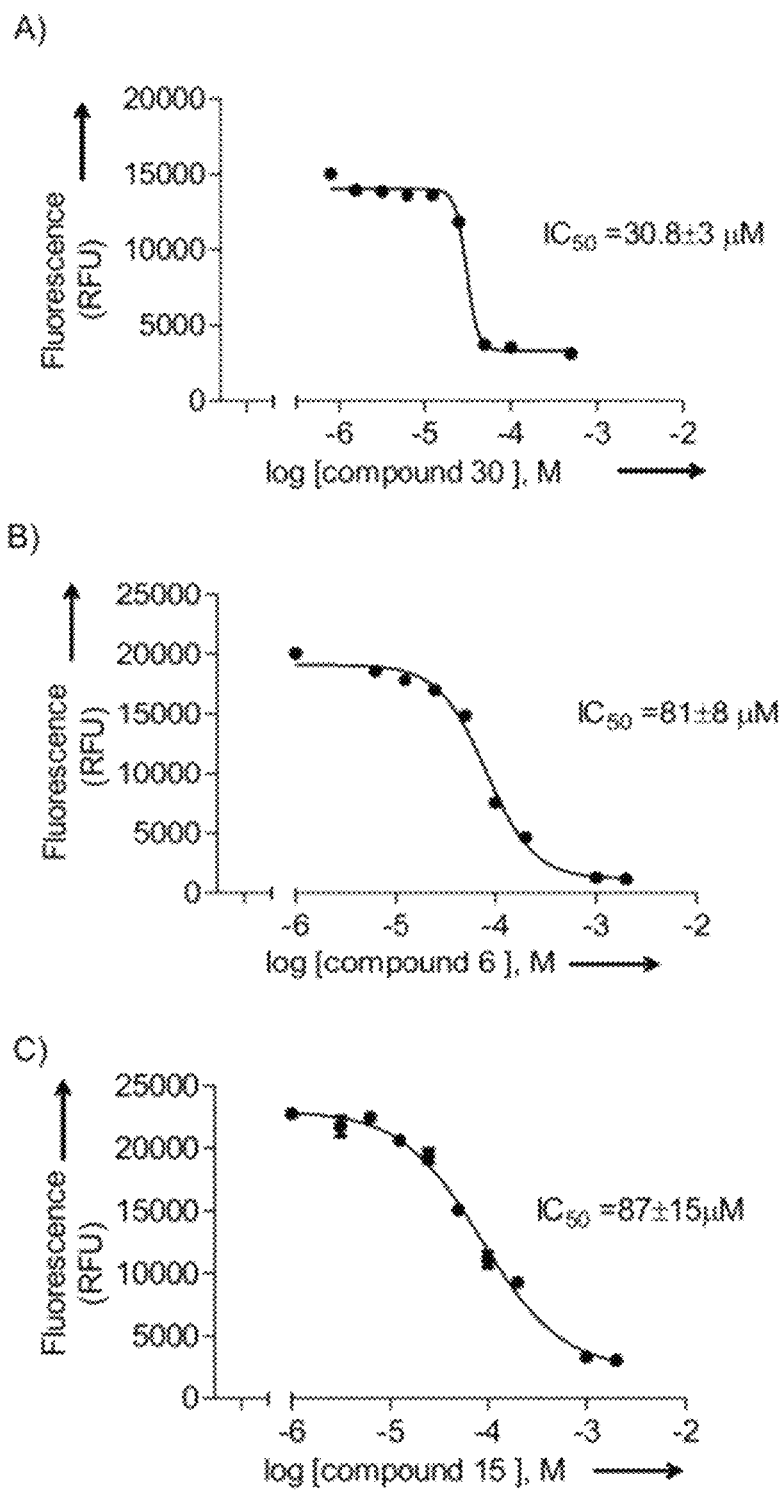

FIG. 5. Cell proliferation curve treated with compound 30 (A) and 6 (B) and 15 (C).

Figure 6:
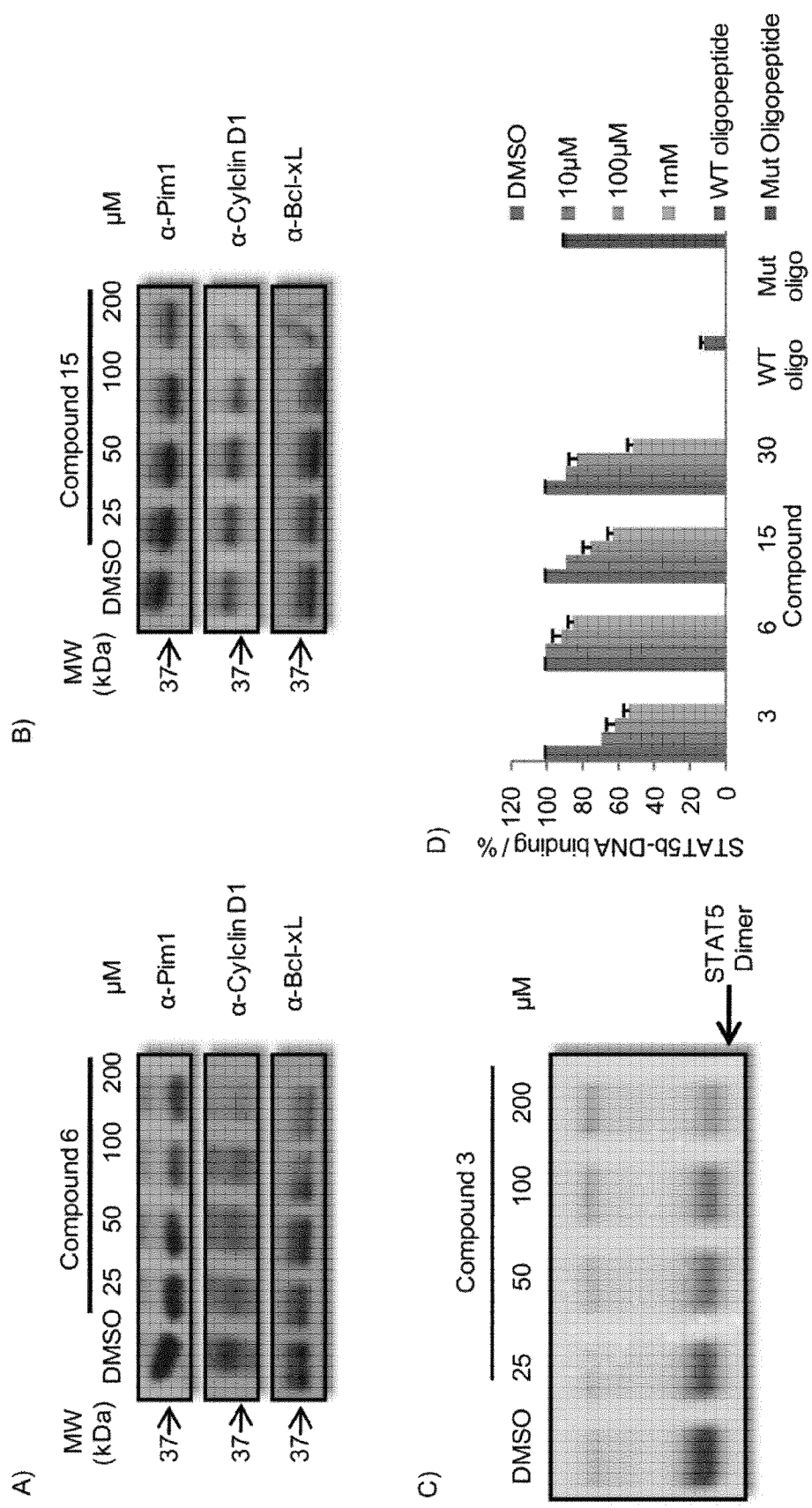

FIG. 6. Expression of downstream targets of STAT5 (Pim1, Cyclin D1 and Bcl-xL) were reduced upon reduction of STAT5 phosphorylation (A and B). (C) Compound 3 inhibits STAT5 dimer DNA-binding activity in BaF3/FLT3-ITD nuclear extract. (D) Effect of compound treatment on the formation of trimeric (STAT5)2-DNA complexes using an ELISA-based STAT5 transcription factor assay kit.

Figure 7:
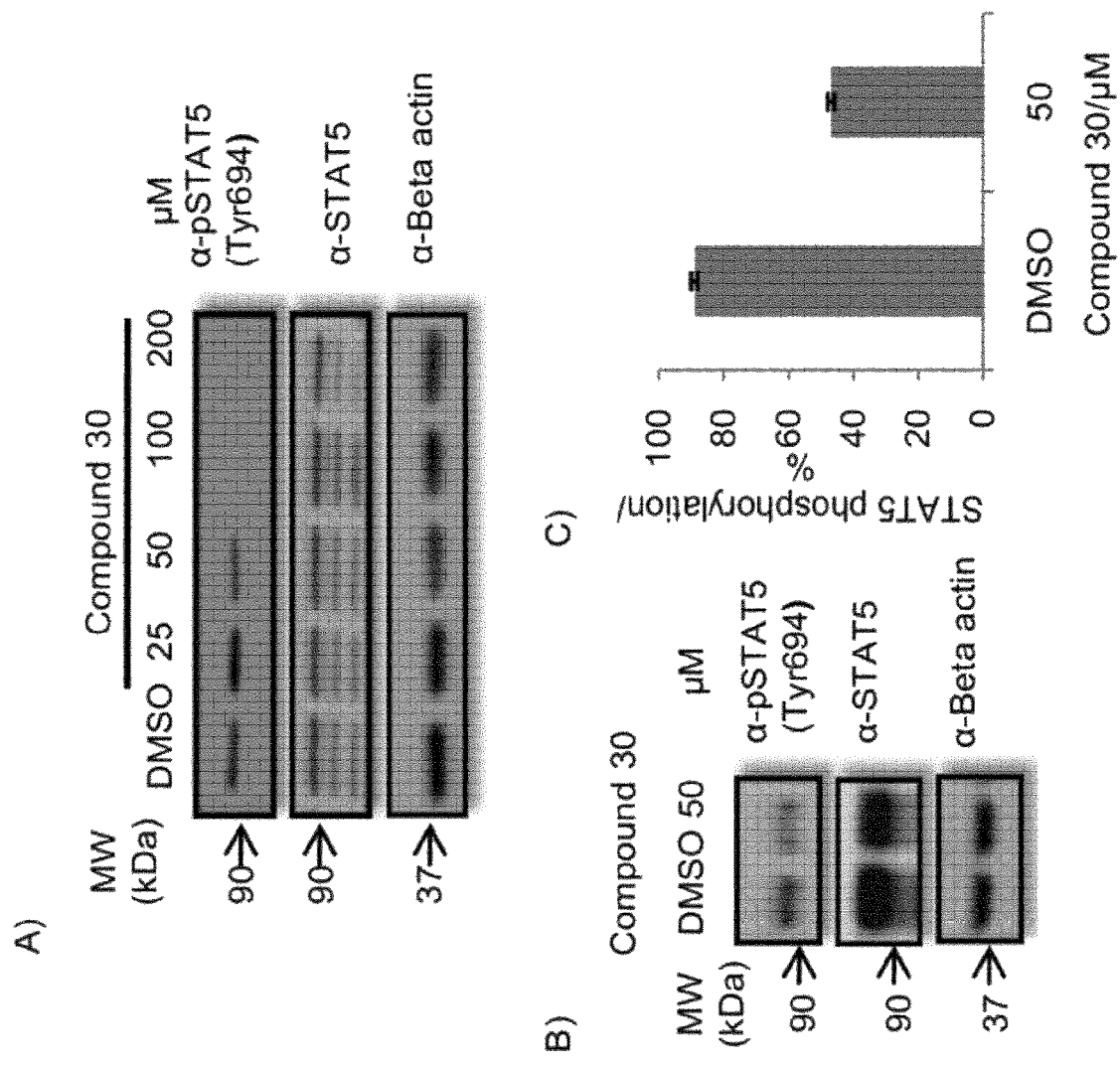

FIG. 7. Compound 30 reduces STAT5 phosphorylation significantly in both BaF3/FLT3-ITD (A) and K562 (B) cells at 50 µM after 6 hrs of incubation. Relative STAT5 phosphorylation levels were plotted (C) after quantification using Image J software (National Institutes of Health, Bethesda, Md.). Experiments were repeated twice; errors bars represent SD.

Figure 8:
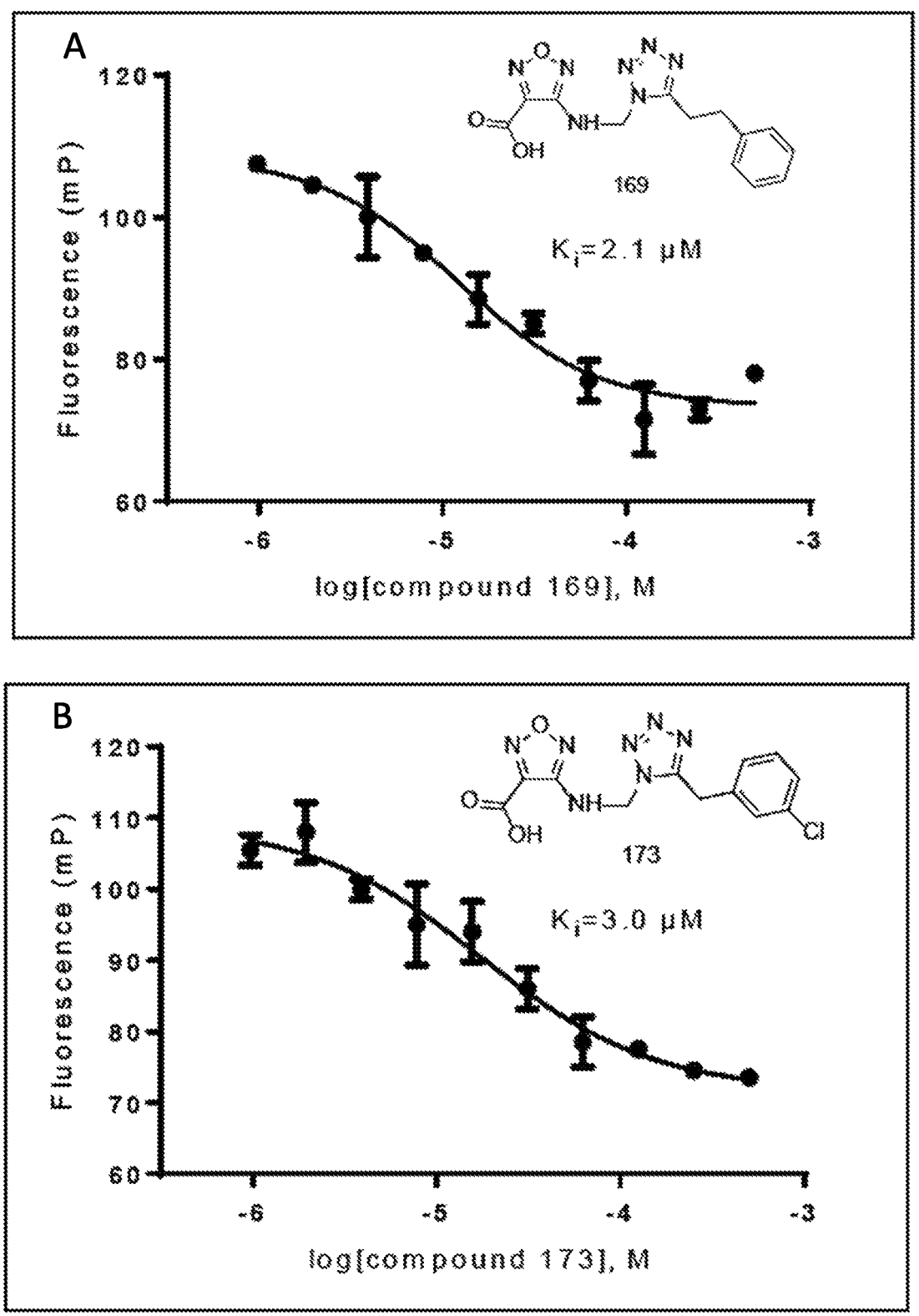
Figure 8:
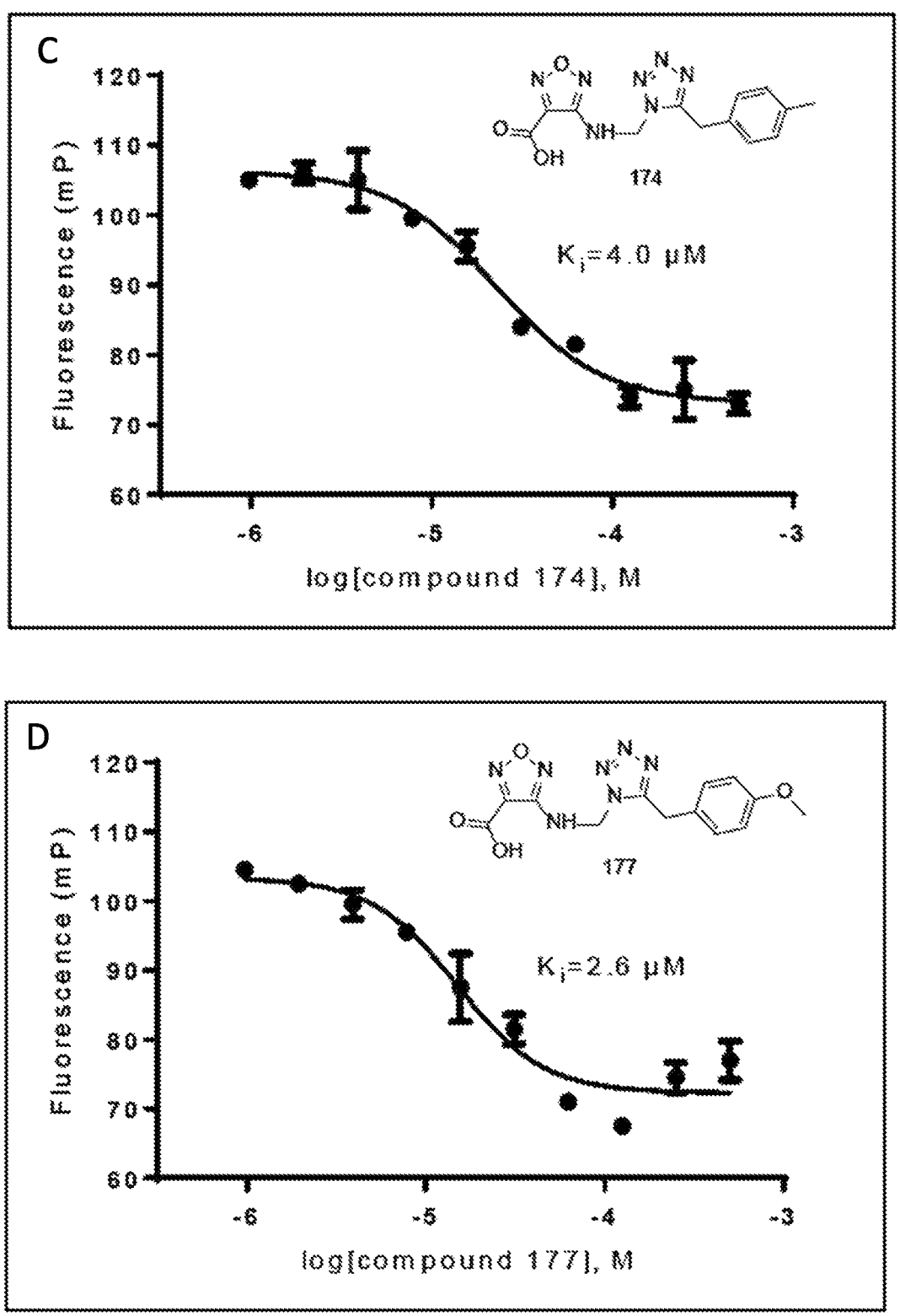
Figure 8:
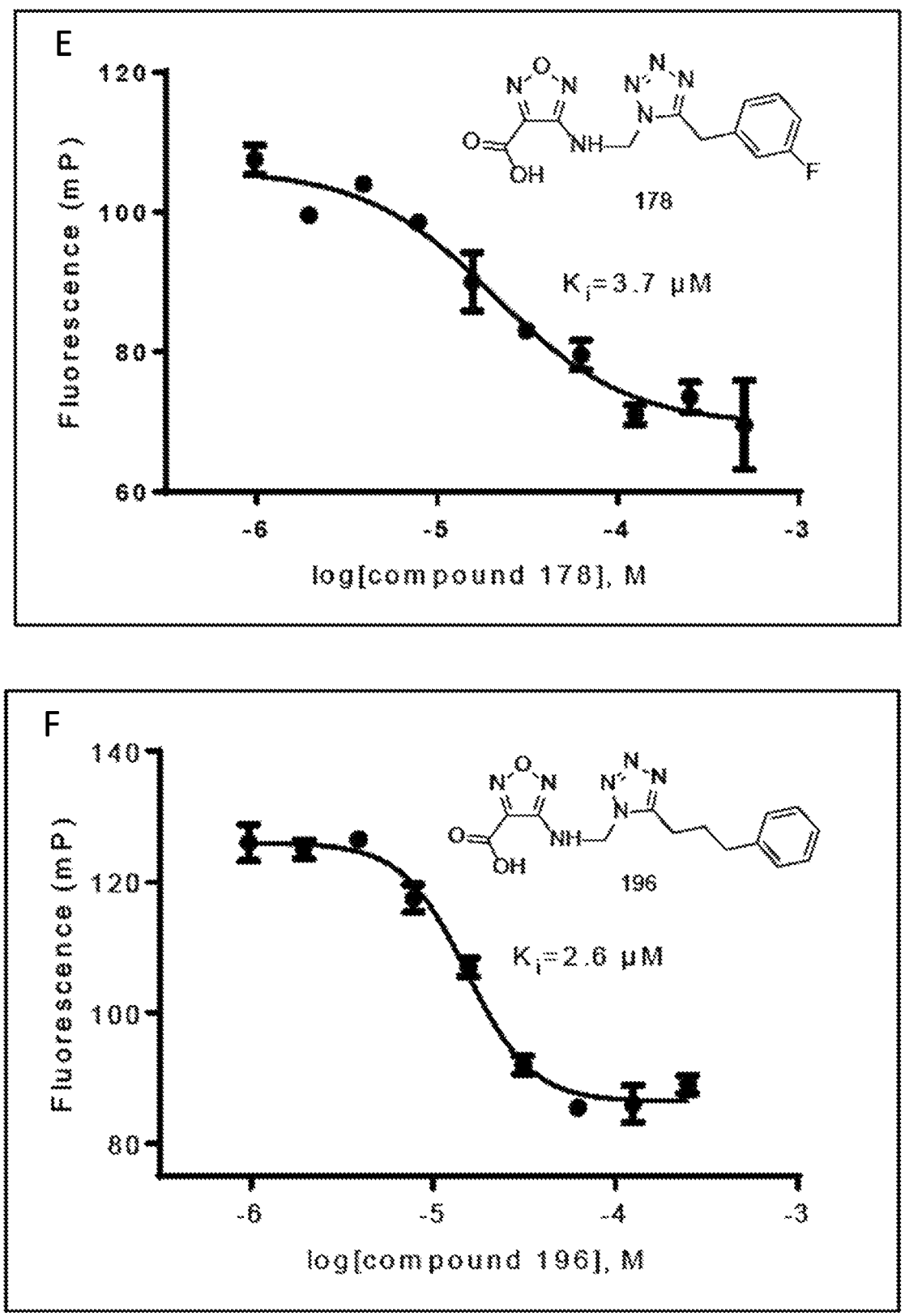
Figure 8:
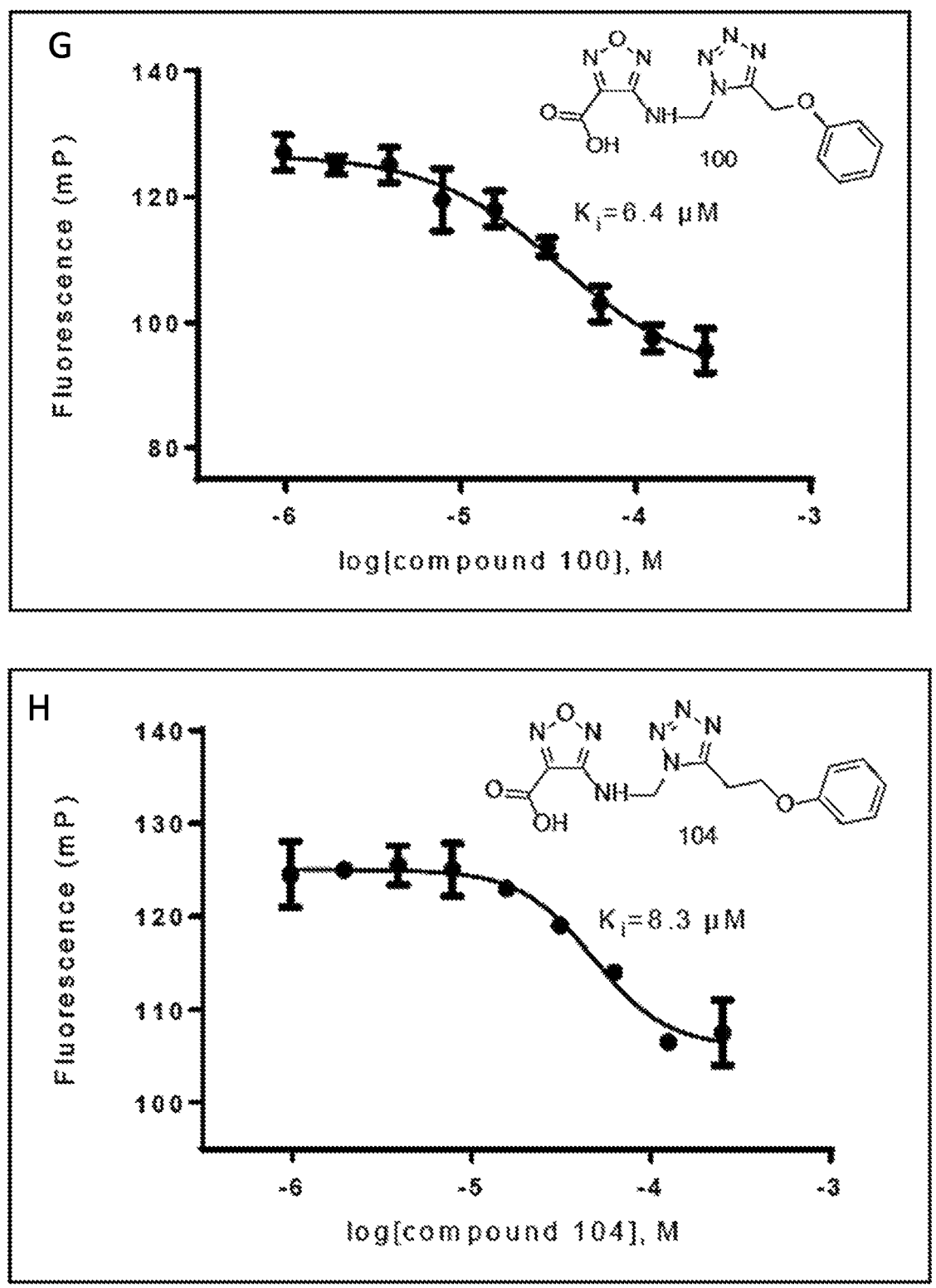
Figure 8:
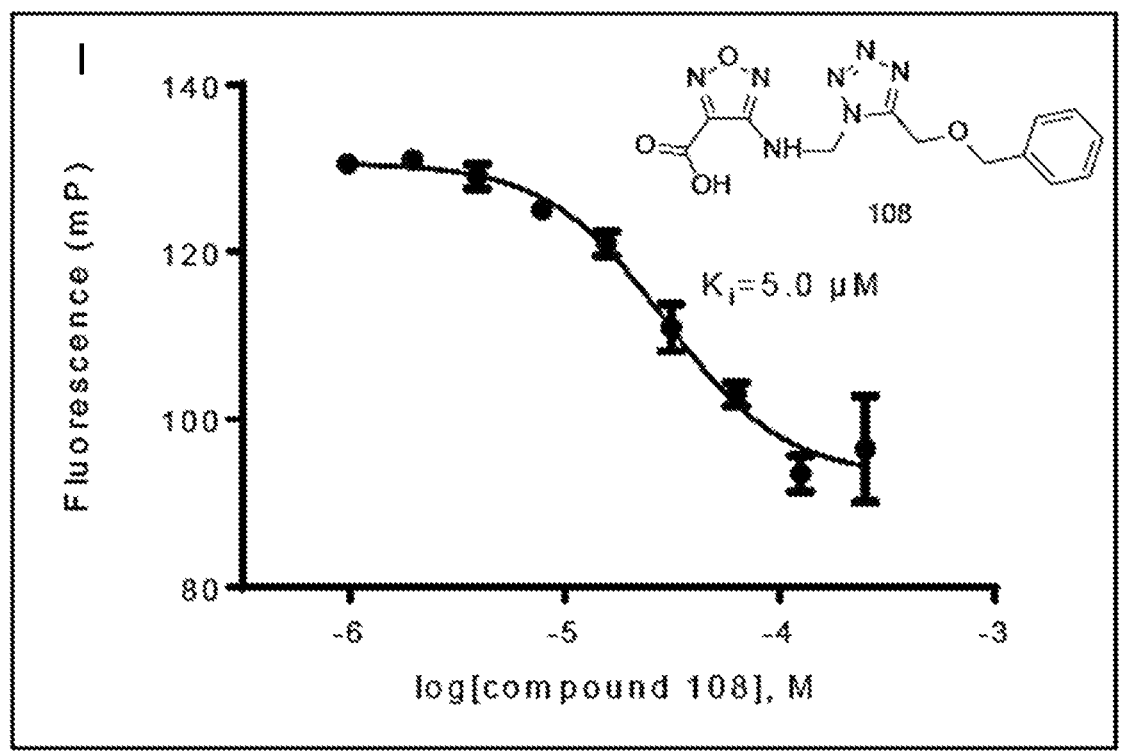
Figure 8:
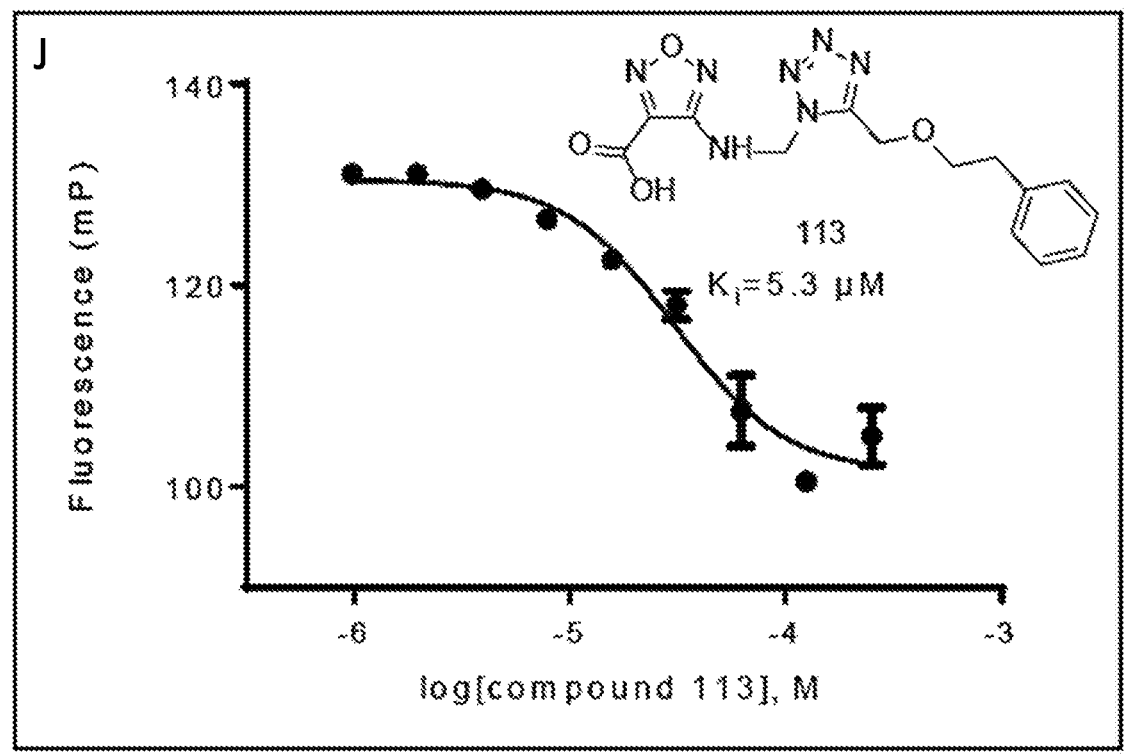

FIG. 8. Cell proliferation curve treated with compound 169 (A), 173 (B), 174 (C), 177 (D), 178 (E), 196 (F), 100 (G), 104 (H), 108 (I), and 113 (J).

Figure 9:
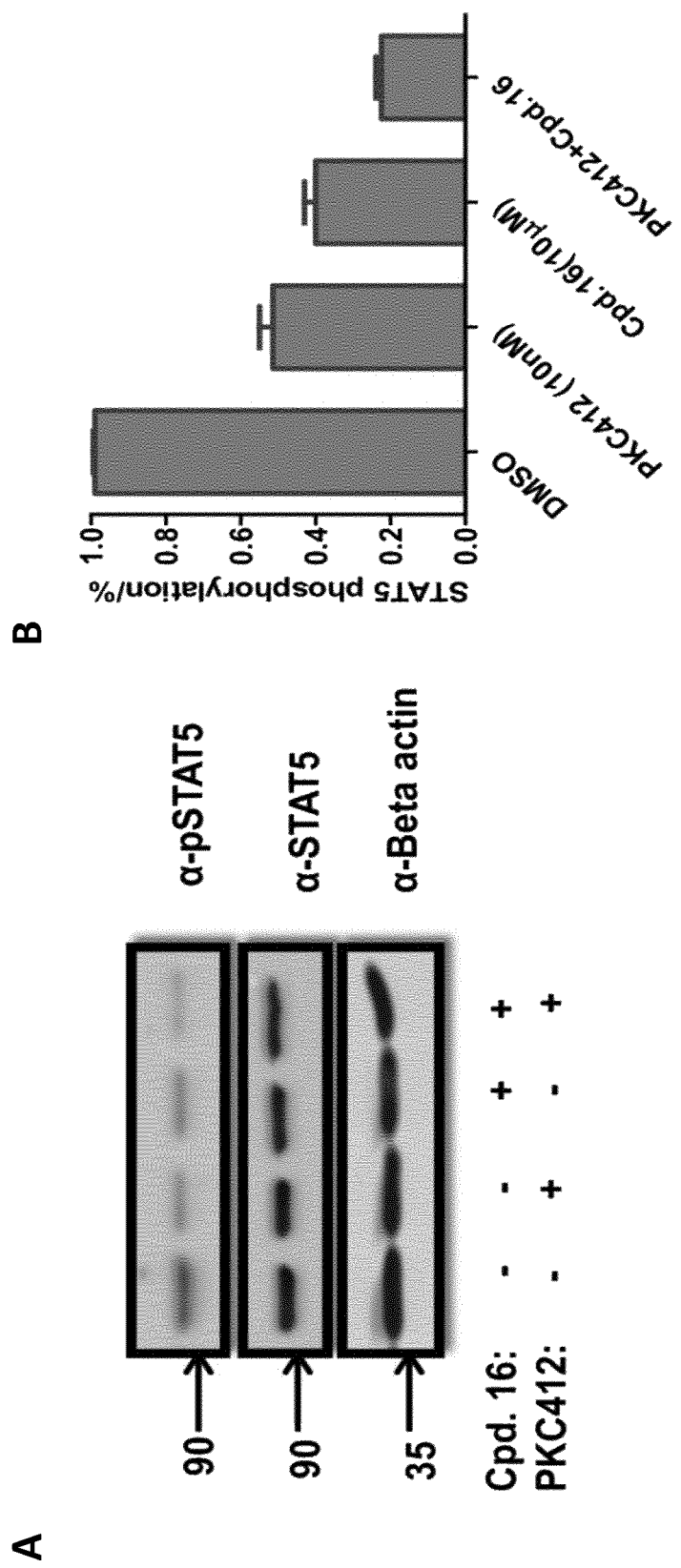

FIG. 9. Compound 16 reduces STAT5 phosphorylation in a synergistic manner in combination with the multi-kinase inhibitor Midostaurin. (A) level of phosphor-STAT5 is shown for control, compound 16, PKC412 and a combination of compound 16 with PKC412. Relative STAT5 phosphorylation levels were plotted (B) after quantification using Image J software (National Institutes of Health, Bethesda, Md.). Experiments were repeated twice; errors bars represent SD.

EXAMPLES

Cytokines and growth factors induce proliferation and differentiation of healthy cells mediated by intracellular phosphorylation cascades. In contrast, cytokine-independent proliferation is a typical molecular characteristic of cancer cells. The pathological cell growth is evoked by genomic DNA mutations, which alter the expression or the activity of receptor tyrosine kinases or of downstream protein kinases. As a consequence, intracellular signaling proteins are constitutively activated. Kinase inhibitors have been developed as a new option for the treatment of cancer during the past decade. These drugs have revolutionized the therapy of certain neoplastic diseases, e.g. chronic myeloid leukemia (CML), in which inhibitors of the kinase BCR/ABL like imatinib have increased patient survival rates impressively. Unfortunately, mutations in the target kinases can abolish the anti-cancer effects of kinase inhibitors and lead to resistant cancer cell lines. Such resistances could be counteracted pharmacologically, if intracellular signaling was blocked downstream of kinases, e.g. at the level of transcription factors.

STAT proteins (signal transducers and activators of transcription) are transcription factors representing central hubs in the signaling of numerous cancer cell types. For example, in >95% of CML patients and >60% of patients suffering from acute myeloid leukemia (AML) STAT5 has been identified as the direct downstream target of mutated kinases. In these cases of CML and AML, STAT5 proteins are constitutively activated and therefore targeting STAT5 could be a strategy to block cytokine-independent cancer cell amplification while avoiding the appearance of resistance mutations in kinases.

Over the recent years our group has developed methodologies for the sensitive and site-directed detection of protein-binding molecular fragments based on reversible (dynamic) ligation reactions on protein surfaces. The method is able to distinguish enhancing, cooperatively binding fragments, from inhibitory, competitive binders. It has been applied to protein phosphotyrosine phosphatases (PTPs) demonstrating that fragments that enhance the cleavage of the generic PTP substrate 4-formyl-phenyl phosphate 1 target secondary binding sites of these proteins and thus were successful starting points to construct specific inhibitors for these enzyme. In this contribution, we extent this methodology from PTPs toward phosphotyrosine binding domains, exemplified by the SH2-domain of STAT5 (FIG. 1) reporting the discovery of novel phosphotyrosine mimetic fragments as specific inhibitors of STAT5 and their application in a cellular model of AML.

Results and Discussion

STAT5 is expressed in two closely related forms, STAT5a (793 amino acids) and STAT5b (786 amino acids), showing 94% identity of amino acid sequence. The protein associates to the intracellular domains of activated cytokine receptors and becomes phosphorylated at tyrosine 694. Phosphorylated STAT5 (p-STAT5) dimerizes via a Src-homology type 2 (SH2) phosphotyrosine recognition domain and translocates into the cell nucleus. There, p-STAT5 dimers bind to their genomic promoter sequence inducing the transcription of their target genes. STAT proteins have been described as difficult pharmacological targets. While highly potent peptide ligands have been reported for the STAT-SH2 domains, these phosphopeptide mimetics usually fail to provide significant cellular activity. Several small molecule inhibitors of STAT5 have been reported, the most potent molecules are based on salicylic acid and phenyl-di-phosphate as phosphotyrosine mimetics. Binding of fragments to the STAT5-SH2 domain was recorded by measuring the fluorescence polarization of a high-affinity carboxyfluoresceine-labeled phosphotyrosine octapeptide (2) possessing a $K_D$ of 55 nM, which we had developed earlier from a phosphopeptide screen of reported STAT5 recognition sites. The ChemBioNet fragment collection composed in accordance with the substructure composition of the World Drug Index (WDI) was screened both for enhancing and inhibiting fragments of the phosphopeptide-STAT5 interaction. Although several primary amines were identified as enhancing fragments, far stronger effects were observed for inhibitory fragments that were able to block the interaction of the high-affinity probe with and without the electrophilic phosphotyrosine mimic (1).

One fragment, the 4-(1H-tetrazol-1-yl-methyl-amino)-furazan-3-carboxylic acid (3) displayed a ligand efficiency of 2.23 kJ/mol per non-hydrogen atom, significantly higher than that of the phosphotyrosine mimetic (1), the nanomolar phosphopeptide (2) and all reported STAT5 inhibitors. Indeed ligands with such a high binding efficiency are rather found for enzymatic binding pockets than for protein-protein interaction sites. To rationalize this surprising observation, potential binding modes of the phosphotyrosine and the fragment hit (3) were considered using the published crystal structure of STAT5 (FIG. 2). The phosphotyrosine binding site in the STAT5-SH2 domain is shallow compared to the deeper binding pockets of PTP, coordinating the tyrosine phosphate by only two H-bonding amino acid residues, Arg618 and Ser622. As a result, the benzene ring of the ligand is not buried in a cavity like in the case of PTPs but rather exposed to the solvent at the protein surface.

Binding of the furazan-carboxylate (3) is mediated by the Coulomb interaction between the carboxylate anion of (3) and the cation of protonated Arg618 and three essential H-bonds involving Arg618 and Ser 622. Several additional H-bonds are predicted by the binding model, between the 4-amino group of (3) and the carbonyl of Asn642, the tetrazole ring of the ligand and the amide-$NH_2$ of Asn642, and an internal H-bond within the ligand that might stabilize the binding conformation of the ligand. Derivatives of fragment (3) were synthesized and tested in order to investigate structure-activity relations and, thus, to challenge and substantiate the binding hypothesis (Tables 1, 2). The 4-amino-furazan-3-carboxylate fragment (4), which was prepared from ethyl 2-cyano acetate in two steps (Scheme 1), was inactive even at mM concentrations. The same was observed for the 1H-tetrazole (5).

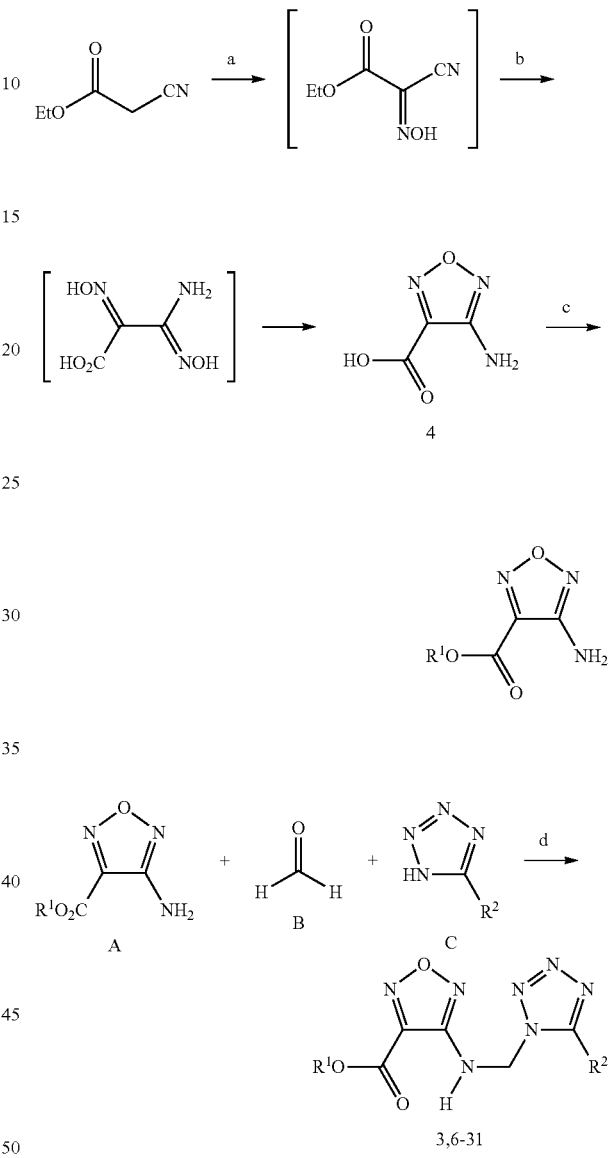

Scheme 1. Synthesis of tetrazole derivatives 3,6-31

Reaction conditions: a) $NaNO_2$, $H_3PO_4$, $H_2O$/EtOH, 10° C., 12 h. b) NaOH, KOH, $NH_2OH*HCl$, HCl, 66%. c) $R_1OH$, $H_2SO_4$, reflux, 12 h, 90-95%. d) A (1.0 eq.), B (2.0 eq.), C (1.5 eq.), MeCN, AcOH, rt, 16 h.

Combinations of one 4-amino furazan fragment A with various heterocycles were prepared in a three-component reaction with formaldehyde B and the tetrazole component C. Ester derivatives of (3) were prepared using the same synthetic approach with furazan carboxylate esters as starting materials. Methyl ester (6) was active with a significant reduction of the $K_D$ value to 76 μM, the n-butyl ester (7) was further deactivated with 145 μM affinity. On the contrary, the 1-acetoxy-1-ethyl carboxylate (15) exhibited a lower $K_D$ of 14 μM. Next, variations of the furazan and of the linker motif between the two heterocycles were investigated. Replacement of the oxygen in the furazan ring by sulfur yielded the inactive 1, 2, 5-thiadiazole (8).

TABLE 1

Inhibitors of STAT5b

| Cpd # | Structure | $K_I$ (μM) | LE (kJ/mol* atom#) |
|---|---|---|---|
| 1 | (phosphate-O-phenyl-CHO) | >500 | n.a. |
| 2 | Fluo-GY*LSLPPW-NH2 | 0.055 ± 0.006 | 0.42 |
| 3 | (furazan-COOH with NH-CH2-tetrazole) | 1.4 ± 0.5 | 2.23 |
| 4 | (furazan with COOH and NH2) | 419.5 ± 2.14 | 2.14 |
| 5 | (1,2,3-triazole-H) | >500 | n.a. |
| 6 | (furazan-COOMe with NH-CH2-tetrazole) | 37.4 ± 1.2 | 1.58 |
| 7 | (furazan-COO$^n$Bu with NH-CH2-tetrazole) | 48.2 ± 5 | 1.30 |
| 8 | (thiadiazole-COOMe with NH-CH2-tetrazole) | >500 | n.a. |
| 9 | (furazan-COOH with NH-CH2-triazole) | 190.6 ± 24 | 1.41 |

TABLE 1-continued

Inhibitors of STAT5b

| Cpd # | Structure | $K_I$ (μM) | LE (kJ/mol* atom#) |
|---|---|---|---|
| 10 | 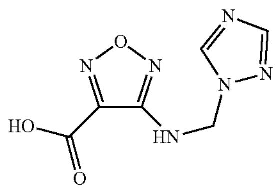 [SMILES: O=C(O)c1nonc1NCn1cncn1] | 47.5 ± 8.5 | 1.64 |
| 11 | 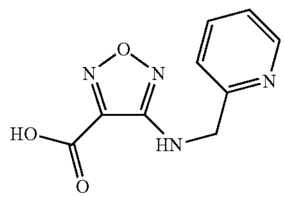 [SMILES: O=C(O)c1nonc1NCc1ccccn1] | >500 | n.a. |
| 12 | 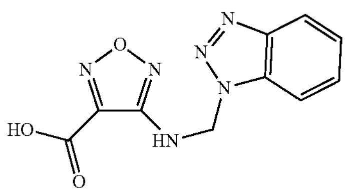 [SMILES: O=C(O)c1nonc1NCn1nnc2ccccc21] | 188.5 ± 25 | 1.12 |
| 13 | 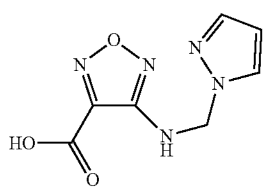 [SMILES: O=C(O)c1nonc1NCn1cccn1] | 121.8 ± 7.3 | 1.49 |
| 14 | 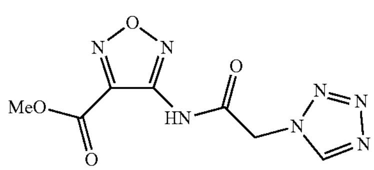 [SMILES: COC(=O)c1nonc1NC(=O)Cn1cnnn1] | >500 | n.a. |
| 15 | 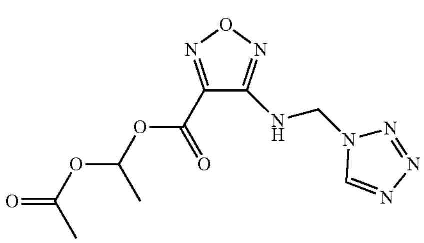 [SMILES: CC(=O)OC(C)OC(=O)c1nonc1NCn1cnnn1] | 4.6 ± 1.7 | 1.45 |

Conversion of IC50 values into KI values was carried out as described and ligand efficiency was calculated using the equation derived. n.a. = not applicable

TABLE 2

STAT5 inhibitors with 5-substituted tetrazole rings 17-31 (for structures see Scheme 1):

| Cpd # | $R^1$ | $R^2$ | $K_I$ (μM) | LE (kJ/mol *atom#) |
|---|---|---|---|---|
| 16 | H | Ph | 1.4 ± 0.3 | 1.59 |
| 17 | Me | Ph | 37.1 ± 6 | 1.15 |

TABLE 2-continued
STAT5 inhibitors with 5-substituted tetrazole rings 17-31 (for structures see Scheme 1):
| Cpd # | R¹ | R² | $K_I$ (μM) | LE (kJ/mol *atom#) |
|---|---|---|---|---|
| 18 | Me | 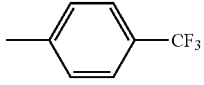 | 94.9 ± 2.1 | 0.88 |
| 19 | H | 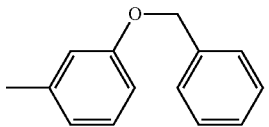 | 1.2 ± 0.5 | 1.16 |
| 20 | Me | 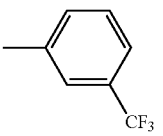 | 9.5 ± 1.8 | 1.10 |
| 21 | H | 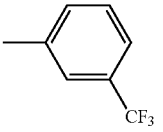 | 0.86 ± 0.05 | 1.38 |
| 22 | Me | 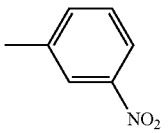 | >500 | n.a. |
| 23 | Me | 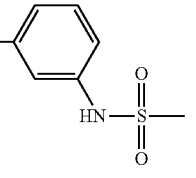 | 18.3 ± 2.4 | 1.00 |
| 24 | Me | 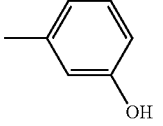 | 22.3 ± 3 | 1.21 |
| 25 | Me | 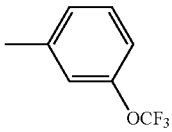 | 16.7 ± 4.3 | 1.01 |
| 26 | H | 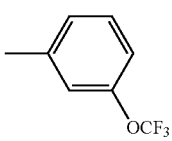 | 3.0 ± 0.7 | 1.21 |
| 27 | H | 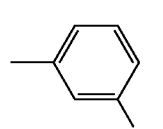 | 0.62 ± 0.09 | 1.61 |

TABLE 2-continued

STAT5 inhibitors with 5-substituted tetrazole rings 17-31 (for structures see Scheme 1):

| Cpd # | $R^1$ | $R^2$ | $K_I$ (μM) | LE (kJ/mol *atom#) |
|---|---|---|---|---|
| 28 | H | –⟨C₆H₄⟩–F (para) | 3.4 ± 1.2 | 1.42 |
| 29 | H | –⟨C₆H₄⟩–⟨C₆H₅⟩ (biphenyl) | 0.8 ± 0.2 | 1.30 |
| 30 | H | –CH₂–⟨C₆H₅⟩ | 8.6 ± 2 | 1.31 |
| 31 | H | –CH₂–⟨C₆H₄⟩–F (para) | 7.2 ± 1.9 | 1.28 |

Conversion of IC50 values into KI values was carried out as described and ligand efficiency was calculated using the equation derived.

Numerous variations of the tetrazole part of the molecule were conducted. While the 1,2,3-triazol-1-yl (9), the 1,2,4-triazol-1-yl (10), the pyridin-2-yl (11), and the 1,2,3-benzotriazol-1-yl (12) were completely inactive, the pyrazol-1-yl derivative (13) was active in the micromolar range with a $K_D$ of 122 μM. Replacement of the aminomethylene bridge by an acetamide linkage (14) abolished the activity as well. Interestingly, the 5-position of the tetrazol ring in (3) could be substituted with a phenyl ring retaining the activity toward STAT5 both for the free acid (16, 1.4 μM) and for the methyl ester (17, 37 μM) (Table 2). Most of the derivatives substituted at the phenyl ring in p- or m-position displayed improved binding to the SH2 domain of STAT5, submicromolar affinities were found for the m-trifluoromethyl-(21, 0.86 μM), the m-fluoro-(27, 0.62 μM) and the biphenyl derivatives (29, 0.8 μM).

Specificity of fragment (3) was investigated both with respect to the closely related SH2 domain of STAT3 and to the protein tyrosine phosphatase SHP2. No inhibition of SHP2 and no binding of to the SH2 domain of STAT3 were detected at concentrations up to 1 mM. Sequence alignment of the SH2 domains of STAT3 and 5 revealed that asparagine Asn642, the amino acid being crucial for the hydrogen bond network depicted in FIG. 2, is only present in STAT5-SH2, while Arg618 and Ser622 are retained in STAT3-SH2, thereby explaining the surprisingly high specificity of fragment (3).

Biological Evaluation

Having established the structure-activity relations of the novel fragment inhibitors of STAT5, the biological activity was studied in a cellular disease model. For the purpose, the murine pro-B-cell line BaF3 was used stably transfected with the full-length cDNA sequence of the human FLT3 receptor, carrying an internal tandem duplication (ITD) mutation of 10 amino acids (Mizuki et al.: Flt3 mutations from patients with acute myeloid leukemia induce transformation of 32D cells mediated by the Ras and STAT5 pathways. Blood 2000, 96, 3907-3914). By this mutation the juxtamembrane domain of FLT3 loses its inhibitory interaction with the two adjacent tyrosine kinase domains enabling their auto-phosphorylation. In consequence, in the FLT3-ITD transfected cells STAT5 is constitutively phosphorylated and does not require the cytokine interleukin-3 for activation. As the FLT3-ITD mutation is found in up to 35% of all patients suffering from AML, thus, it can be considered as a relevant model for this disease (see e.g. Kindler et al: FLT3 as a therapeutic target in AML: still challenging after all these years. Blood 2010, 116, 5089-5102).

At first, the ligand-mediated inhibition of STAT5 phosphorylation at conserved tyrosine residues (Tyr694 and Tyr699) was investigated, which is initiated by the binding of the SH2 domain to phosphorylated cell surface receptors. Compounds (3), (6), (15) and (30) were dissolved in DMSO (20 mM) and added to BaF3/FLT3-ITD cells suspended in RPMI-medium supplemented with 10% (v/v) fetal calf serum. After 6 h cells were harvested to determine the level of STAT5 phosphorylation using phosphotyrosine-specific antibodies (FIGS. 4A-B). The strongest inhibitory effect was observed for the methyl ester fragment (6) with a clear reduction of STAT5 phosphorylation already at a concentration of 25 μM and with an $IC_{50}$ value of 44.2 μM. A similar effect was observed for the acetoxy-ethyl-carboxylate (15) displaying an $IC_{50}$ of 68.9 μM. (FIGS. 4C, F)

Both compounds (6) and (15) had no effect on the overall the expression of endogenous STAT5. In contrast, the phosphorylation of STAT5 was inhibited by the free acid fragment only with an $IC_{50}$ value of >100 μM (see FIG. S6F). We suspected that the low cellular activity of (3) is due to the low cellular uptake of this compound, which might be hampered by its high polarity (c log P=1.11). This consideration was substantiated by the significantly more active nonpolar derivatives (6) and (15), which are likely to be cleaved enzymatically by intracellular esterases and thus act as prodrugs. The selectivity of compounds (6) and (15) in cells were investigated, too, and both showed only negligible effects on STAT3 phosphorylation and on endogenous STAT5 expression (see FIGS. S7A, B), suggesting that the inhibitory effects were STAT5-specific in cells, too.

The highest cellular activity was found for compound (30), which was the first free acid fragment showing strong inhibition of STAT5 phosphorylation with an $IC_{50}$ of 30.8

µM (FIG. 5A) and displayed strongly improved solubility compared to the 5-aryl-substituted tetrazole. Compound (30) shows a clear reduction on STAT5 phosphorylation at 50 µM in both BaF3/FLT3-ITD and K562 cells after 6 h of incubation. (FIGS. 7A, B). Next, the functional effects of STAT5 inhibitors (6) and (15) on cellular transcription were investigated. For the purpose, the expression of three transcriptional targets of STAT5, namely Pim1 kinase, cyclin D1 and Bcl-xl, which play essential roles in cell cycle progression and survival, was monitored by Western Blotting (FIGS. 6A, B). Treatment of BaF3/FLT-ITD cells with (6) or (15) resulted in a dose dependent reduction of Pim1, cyclin D1 and Bcl-xL expression after 6 h, indicating the disruption of STAT5 activation and the abolishment of the transcriptional activity of STAT5.

Having proven the functional inhibition of STAT5 as a transcription factor, the effect of STAT5 inhibitors on the proliferation of cancer cells carrying the common FLT3-ITD mutation was investigated. Cells were incubated for 48 h and cell proliferation was quantified by the Alamar blue assay (FIG. 5). Both compounds, methyl ester (6) and prodrug (15) showed a clear dose-dependent inhibition of cell proliferation. For comparison, we have tested both compounds on non-STAT5-dependent cell lines and the cytotoxicity effect were negligible up to 500 µM. (FIG. S9).

As an additional confirmation for the mode of action of the STAT5-binding fragments, we finally investigated their potential to interfere directly with the binding of phosphorylated STAT5 dimers to the target DNA sequences of the transcription factor. For the purpose, phosphorylated STAT5 dimers were extracted from nuclei of BaF3/FLT3-ITD cells were incubated with respective compounds for 1 h at room temperature and eventually added to the microtiter plate wells coated with target DNA. STAT5 ligands added to this cell-free assay detecting the formation of protein-dimer-DNA complexes did not have to cross a cell membrane and accordingly in this assay fragment (3) was a more potent inhibitor than compounds (15) and (6), respectively, corresponding to the affinity ranking in the monomer binding assay. Same phenomenon was observed in EMSA, indicating the inhibition effect of fragment (3) on STAT5 dimer formation thereafter affects the STAT5 DNA-binding activity. (FIGS. 6C, D)

In additional experiments, it could be demonstrated that the further compounds of Formulae 100, 104, 108, 113, 169, 173, 174 177 178 and 196 show significant cellular activity (see FIG. 8).

Out of the compound series described in this patent, compound 16 was tested for a possible synergistic antitumor effect with the multi-kinase inhibitor Midostaurin (PKC412; structures shown below).

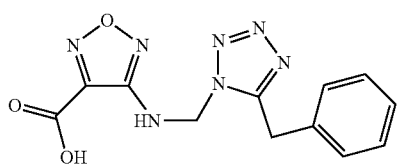
Compound 16

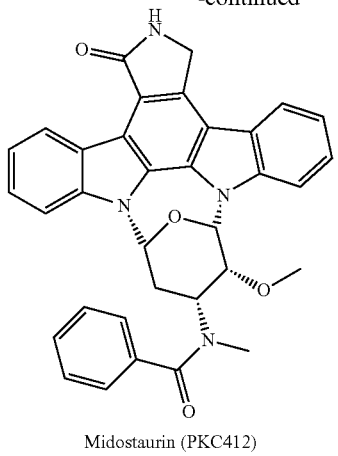
Midostaurin (PKC412)

Both substances were tested in the human leukemia cell line MV-411, either alone or in combination of 10 µM compound 16 and 10 nM Midostaurin. Cells were incubated with the substances alone or in combination for 6 hours. Cells were then extracted, and the protein content immunoblotted for the detection of phospho-STAT5, total-STAT5 and for β-actin (internal control for equal protein loading).

As shown in FIG. 9, a clear reduction of phospho-STAT5 was observed when the substances were individually applied to the cells. A further reduction is clearly visible when both substances are applied in combination (see FIG. 10B).

Experimental Methods

Chemical Procedures.

1. Chemicals as well as dry solvents were purchased from Acros, Alfa Aesar, Fluka, Sigma-Aldrich, VWR and used without further purification or distillation unless otherwise stated. Solution phase reactions were monitored either by LC-MS techniques or by thin layer chromatography (TLC) using Analtech silica gel plates (60 $F_{254}$) and the spots were examined under UV light at 254 nm or stained with developing reagents. LC-MS data were recorded on an Agilent 1100 series chromatography workstation (Agilent Technologies) equipped with a single quadruple mass spectrometer and electrospray ionization (ESI). Eluents A (0.1% formic Acid in Millipore water) and B (0.1% formic Acid in acetonitrile) were used in a linear gradient (5-99% B in 5 min or 30 min for preparative runs). Preparations were carried out on HPLC column (10 µM, 250×20 mm, Grom-SIL 300 ODS-5-ST RP-C18) or on a semi-preparative HPLC column (VP 250/10 Nucleodor 100-5 C18 ec Machery-Nagel) employing individual gradients derived from analytical runs (eluents A and B). Besides the Biotage® Isolera™ Spektra One was used for regular flash purifications with pre-pack flash chromatography cartridges from Biotage® employing individual gradients derived from analytical runs or thin layer chromatography (TLC). HRMS measurements were conducted with an Agilent 6210 ESI-TOF mass spectrometer. Nuclear magnetic resonance (NMR) spectra ($^1$H and $^{13}$C NMR) were recorded on a Bruker AVANCE 300 MHz and 500 MHz instrument and chemical shifts (δ) were measured in parts per million (ppm). Coupling constants (J) are expressed in Hertz (Hz). The following abbreviations are used to describe peak patterns when appropriate: s (singlet), d (doublet), t (triplet), q (quadruplet), m (multiplet), and br (broad). The Biotage® Initator+ system was used for rapid microwave-assisted organic synthesis.

General Synthetic Methods 1.1 Method A:

To a solution of 4-amino-furazan-3-carboxylic acid or methylester (1.0 mmol) and tetrazole (1.2 mmol) in 2.7 mL of acetonitrile (hipersolv chromanorm) and 0.3 mL of acetic acid, formaldehyde (37% solution in water, 2.0 mmol) was added and this reaction mixture was stirred at r.t. for 16 h. After concentration of the reaction mixture the residue was dissolved in 20 mL of dichloromethane and washed with a saturated solution of sodium bicarbonate and brine. The organic phase was dried over sodium sulfate and after filtration the filtrate was evaporated in vacuum. The residue was purified by flash column chromatography.

1.2 Method B:

A solution of 4-amino-furazan-3-carboxylic acid (1.2 mmol), tetrazole (1.0 mmol) and formaldehyde (37% solution, 2.0 mmol) in 2.7 mL of DMF and 0.3 mL of acetic acid was stirred at r.t. for 16 h. The solvents were removed under reduced pressure and the residue was dissolved in hot chloroform. After cooling solids were filtrated off and were washed with chloroform. After evaporation of chloroform the product was obtained. In some cases the product was recrystallized from hot chloroform.

1.3 Method C:

A solution of 4-amino-furazan-3-carboxylic acid (1.2 mmol), tetrazole (1.0 mmol), and formaldehyde (37% aqueous solution, 10.0 mmol) in 2.7 mL of acetonitrile and 0.3 mL of concentrated hydrochloric acid was stirred in a sealed microwave reaction vial at 105° C. in a microwave reactor for 5 h. After cooling the reaction, solids were filtrated off, washed with a small amount of water and dried under reduced pressure. The residue was purified by flash column chromatography.

1.4 Method D:

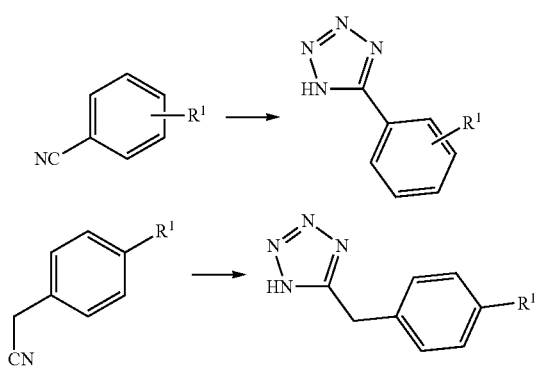

A suspension of the nitrile component (1.0 mmol), NaN$_3$ (2 mmol), and NH$_4$Cl (1.1 mmol) in DMF (5 mL) was stirred in a sealed microwave reaction vial at 140° C. in a microwave reactor for 1 h. After the mixture was evaporated in vacuum, the residue was poured into water and acidified with concentrated HCl to pH=2 and cooled to 5° C. Then the precipitate was filtrated off, washed with cold water, and dried under reduced pressure to give the desired compounds.

4-Formylphenyl-dihydrogen-phosphate [1]

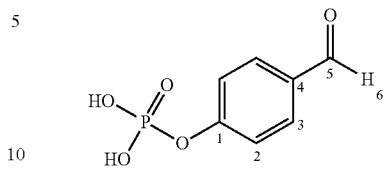

Diethyl chlorophosphate (1.18 mL, 8.19 mmol, 1 eq.) was added dropwise to a cooled (0° C.) solution of 4-hydroxybenzaldehyde (1.0 g, 8.19 mmol, 1 eq.) and triethylamine (1.36 mL, 9.83 mmol, 1.2 eq.) in dry DCM (5 mL) under inert atmosphere. The reaction mixture was warmed to room temperature and stirred furthermore for 3 h. Afterwards the organic phase was extracted with 1 M HCl, saturated NaHCO$_3$, and dried over sodium sulfate and after filtration the filtrate was evaporated in vacuum. The protected phosphate (0.5 g, 1.94 mmol, 1 eq.) and trimethylsilylbromide (0.51 mL, 3.88 mmol, 2 eq.) was stirred in MeCN (5 mL) at room temperature for 6 h. Subsequently the reaction mixture was quenched with 10 mL of H$_2$O/MeOH (1:10), Amberlite® IR120 hydrogen form (4 g) was added and the mixture was stirred at room temperature for 12 h. After filtration and purification by flash column chromatography the product (1) was obtained as white solid (0.254 g, 1.26 mmol, 64%). $^1$H-NMR (500 MHz, DMSO-d$_6$): δ=9.94 (s, 1H, H-6), 7.92 (d, J=8.3 Hz, 2H, H-3), 7.37 (d, J=8.3 Hz, 2H, H-2) ppm. $^{13}$C-NMR (101 MHz, DMSO-d$_6$): δ=192.32 (C-5), 156.36 (C-1), 132.23 (C-4), 132.09 (C-3), 120.94 (C-2) ppm. $^{31}$P-NMR (162 MHz, DMSO-d$_6$): δ=21.3 (m, 1P, P) ppm. HRMS: (ESI): C$_7$H$_7$O$_5$P [M], 202.0031 Da. calcd m/z 200.9953 [M-H]$^-$, found m/z 200.9893 [M-H]$^-$.

4-((1H-Tetrazol-1-yl)-methylamino)-furazan-3-carboxylic Acid [3]

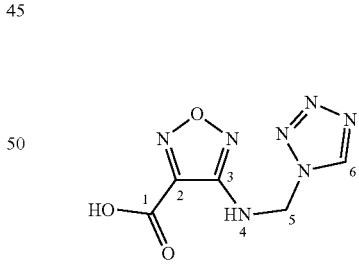

Prepared according to general procedure Method A using 4-amino-furazan-3-carboxylic acid (129 mg, 1.0 mmol, 1.0 eq.), 1H-tetrazol (3.3 mL (0.45M solution), 1.5 mmol, 1.5 eq.) and formaldehyde (0.2 mL, 2.0 mmol, 2.0 eq.) to give the product (3) (184.8 mg, 0.88 mmol) in 88% yield as a white solid. $^1$H NMR (300 MHz, DMSO-d$_6$): δ=9.43 (s, 1H, H-6), 7.90 (t, J=6.9 Hz, 1H, H-4), 5.91 (d, J=6.9 Hz, 2H, H-5) ppm. $^{13}$C-NMR (75 MHz, DMSO-d$_6$): δ=159.7 (C-1), 155.2 (C-2), 144.1 (C-3), 140.3 (C-6), 56.6 (C-5) ppm. HRMS: (ESI): C$_5$H$_5$N$_7$O$_3$ [M], 211.0454 Da. calcd m/z 210.0376 [M-H]$^-$, found m/z 210.0397 [M-H]$^-$.

4-Amino-furazan-3-carboxylic Acid [4]

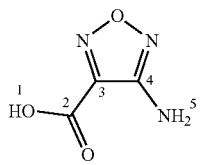

To a stirred suspension of ethyl cyanoacetate (28.3 g, 0.25 mol, 1 eq.) and sodium nitrite (17.3 g, 0.25 mol, 1.0 eq.) in a mixture of EtOH (17 mL) and water (200 mL) was added dropwise 85% $H_3PO_4$ (10 mL) at 10-15° C. and stirred for 12 h. Afterwards the reaction mixture was treated with NaOH (4×10 g, 1 mol, 4 eq.) and KOH (2×14 g, 0.5 mol, 2.0 eq.). To the resulting solution $NH_2OH \cdot HCl$ (69.5 g, 1.0 mol, 4.0 eq.) was slowly added at room temperature and heated up to 95° C., stirred for 2 h, cooled to ambient temperature and quenched with conc. HCl to pH 1. Precipitation occurred on cooling to 0° C. for 12 h and the precipitate was collected by filtration and dried. The filtrate was extracted with diethyl ether (3×30 mL). The combined organic extracts were evaporated under reduced pressure. The residue was combined with the precipitate and recrystallized from hot water to give compound (4) (21.3 g, 0.165 mol, 66%) as white solid. $^1$H-NMR (300 MHz, DMSO-$d_6$): δ=9.69 (br s, 1H, H-1), 6.24 (s, 2H, H-5) ppm. $^{13}$C-NMR (75 MHz, DMSO-$d_6$): δ=162.5 (C-2), 157.1 (C-3), 144.9 (C-4) ppm. HRMS: (ESI): $C_3H_3N_3O_3$ [M], 129.0174 Da. calcd m/z 128.0096 [M-H]$^-$, found m/z 128.0106 [M-H]$^-$.

Methyl 4-((1H-tetrazol-1-yl)-methylamino)-furazan-3-carboxylate [6]

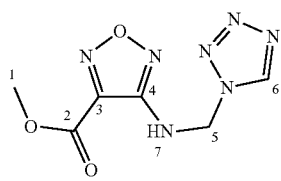

Prepared according to general procedure Method A using 4-amino-furazan-3-carboxylic acid methylester (143 mg, 1.0 mmol, 1.0 eq.), 1H-tetrazol (3.3 mL (0.45M solution), 1.5 mmol, 1.5 eq.) and formaldehyde (0.2 mL, 2.0 mmol, 2.0 eq.) to give the product (6) (184.8 mg, 0.88 mmol) in 88% yield as a white solid. $^1$H NMR (300 MHz, DMSO-$d_6$): δ=9.44 (s, 1H, H-6), 8.01 (t, J=6.9 Hz, 1H, H-7), 5.92 (d, J=6.9 Hz, 2H, H-5) ppm. $^{13}$C-NMR (75 MHz, DMSO-$d_6$): δ=159.5 (C-2), 155.6 (C-3), 144.6 (C-4), 126.2 (C-6), 53.9 (C-5), 53.8 (C-1) ppm. HRMS: (ESI): $C_6H_7N_7O_3$ [M], 225.0610 Da. calcd m/z 248.0508 [M+Na]$^+$, found m/z 248.0510 [M+Na]$^+$. $^1$H NMR (300 MHz, CDCl$_3$): δ=8.97 (s, 1H, H-6), 7.98 (t, J=7.0 Hz, 1H, H-7), 6.08 (d, J=7.1 Hz, 2H, H-5), 4.00 (s, 3H, H-1) ppm. $^{13}$C-NMR (75 MHz, CDCl$_3$): δ=161.2 (C-2), 159.6 (C-3), 143.2 (C-4), 135.9 (C-6), 55.4 (C-1), 53.2 (C-5) ppm. HRMS: (ESI): $C_6H_7N_7O_2S$ [M], 241.2290 Da. calcd m/z 264.2188 [M+Na]$^+$, found m/z 264.0288 [M+Na]$^+$.

1-Acetoxyethyl 4-((1H-tetrazol-1-yl)-methylamino)-furazan-3-carboxylate [15]

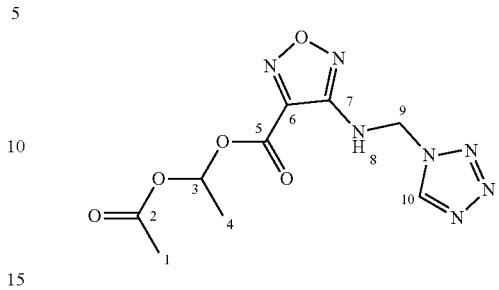

To a stirred solution of 4-(OH-tetrazol-1-yl)methylamino)-furazan-3-carboxylic acid (100 mg, 0.47 mmol, 1.0 eq.) and DIPEA (0.16 mL, 0.94 mmol, 2 eq.) in DMF (2 mL) was added 1-bromoethyl-acetate (156 mg, 0.94 mmol, 2 eq.) and the reaction was stirred for 18 h at room temperature. The reaction mixture was evaporated in vacuum and purified by flash column chromatography to give the product (15) (63.7 mg, 0.21 mmol) in 45% yield as a brownish oil. $^1$H NMR (500 MHz, DMSO-$d_6$): δ=9.44 (s, 1H, H-10), 8.02 (t, J=6.9 Hz, 1H, H-8), 7.04 (q, J=5.5 Hz, 1H, H-3), 5.93 (d, J=6.9 Hz, 2H, H-9), 2.09 (s, 3H, H-1), 1.57 (d, J=5.5 Hz, 3H, H-4) ppm. $^{13}$C-NMR (126 MHz, DMSO-$d_6$): δ=169.03 (C-5), 156.90 (C-2), 155.76 (C-7), 144.48 (C-6), 139.22 (C-10), 89.85 (C-3), 56.97 (C-9), 20.98 (C-4), 20.75 (C-1) ppm. HRMS: (ESI): $C_9H_{11}N_7O_5$ [M], 297.0822 Da. calcd m/z 320.0719 [M+Na]$^+$, 336.0459 [M+K]$^+$, found m/z 320.0730 [M+Na]$^+$, 336.0470 [M+K]$^+$.

4-((5-Benzyl-1H-tetrazol-1-yl)-methylamino)-furazan-3-carboxylic Acid [30]

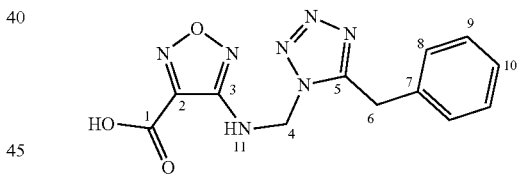

Prepared according to general procedure Method C using 4-amino-furazan-3-carboxylic acid (80.2 mg, 0.62 mmol, 1.2 eq.), 5-benzyl-1H-tetrazole (100.0 mg, 0.52 mmol, 1.0 eq.) and formaldehyde (0.47 mL, 5.2 mmol, 10.0 eq.) to give the product (30) (81.3 mg, 0.27 mmol) in 52% yield as a off white solid. $^1$H NMR (500 MHz, DMSO-$d_6$): δ=7.9 (t, J=6.6 Hz, 2H, H-11), 7.27 (d, J=7.0 Hz, 2H, H-8), 7.25-7.22 (m, 3H, H-9, H-10), 5.89 (d, J=6.6 Hz, 2H, H-4), 4.48 (s, 2H, H-6) ppm. $^{13}$C-NMR (126 MHz, DMSO-$d_6$): δ=159.99 (C-1), 155.42 (C-2), 154.9 (C-5), 140.28 (C-3), 135.65 (C-7), 129.17 (C-8), 128.93 (C-9), 127.34 (C-10), 56.36 (C-4), 28.57 (C-6) ppm. HRMS: (ESI): $C_{12}H_{11}N_7O_3$ [M], 301.0923 Da. calcd m/z 300.0845 [M-H]$^-$, found m/z 300.0805 [M-H]$^-$.

Molecular Docking

The homology model of human STAT5b based on the amino acid sequence of human STAT5a has been described previously. In order to rationalize the binding of the synthesized compounds in the active site of HuSTAT5b model, docking calculations were performed using Surflex-Dock interfaced within Sybyl-X 1.3. The 20 resulting docking conformations were ranked according to the CScore and checked visually in order to choose the most favorable binding conformation.

Expression of STAT5b

The clone for Stat5b expression was kindly provided by Thorsten Berg (MPI, Martinsried). Expression of that truncated version of Stat5b (aa 136-703) cloned into a modified pQE70, with N-terminal MBP-tag and C-terminal His-tag was conducted on autoinduction medium (overnight express/Novagen). Cells were grown to an optical density (O.D.) of 0.3 at 37° C., then the temperature was reduced to 20° C. for further 48 h of expression. Comparable soluble expression levels were obtained with Rosetta2 (DE3) and BL21 (DE3) pLysS (both Novagen). The protein was purified by Ni-chelating chromatography followed by gel filtration (Superdex 200/10 mM HEPES pH 7.8, 100 mM NaCl, 1 mM EDTA, 1 mM DTT, 10% glycerol). A yield of 15 mg MBP-Stat5b-His per liter of culture was obtained and aliquots (200 μl of 3.2 mg/ml) were quick-frozen and stored at −80° C., ready for use.

High-Throughput Screening and Fluorescence Polarization Assays 17000 compounds from the (FMP) ChemBioNet library were tested in a competitive-based fluorescence polarization (FP) assay to investigate the ability of compounds to bind to STAT5b-SH2 domain by displacing respective fluorophore-labeled peptides (5-carboxyfluorescein-GY ($PO_3H_2$) LSLPPW-$NH_2$). The peptide purity was >95% and the screening were performed at room temperature. The final concentration of buffer components used was 10 mM HEPES (pH 7.5), 1 mM EDTA, 0.1% Igepal CA-630, 50 mM NaCl, and 5% DMSO. The final concentration of protein used was at 65 nM which correspond to the dissociation constants (Kd) for the individual protein-peptide interactions in assay buffer. The protein was first added to the black 384 well plate (Corning 3676) followed by test compounds and fluorophore-labeled peptide. The plates were centrifuged, and measured using Safire$^2$ well plate reader (Tecan, Crailsheim, Germany) after 15 minutes incubation at room temperature. For specificity analysis, FP assay was conducted with 100 nM GST-tagged, full length human STAT3 protein (SignalChem, Richmond, BC, Canada) and 10 nM fluorophore-labeled peptides (5-carboxyfluorescein-GY ($PO_3H_2$) LPQTV-$NH_2$). The assay buffer contains 50 mM NaCl, 10 mM HEPES (pH 7.5), 1 mM EDTA, 0.01% Triton-X100 and 2 mM dithiothreitol). The test compounds were serial diluted and incubated with STAT3 protein at room temperature for 1 hour followed by 10 nM of fluorophore labeled peptide. Mixture was centrifuged and incubated for 30 minutes at room temperature before measurement were examined using Safire$^2$. For the analysis of the data GraphPad Prism 5 was used. Ligand efficiencies (LE) were calculated using equation derived as followed.

$$LE=-\Delta G°/HA$$

with (ΔG°) is the standard free energy of binding in KJ and HA is the number of non-hydrogen atoms.

Cell Lines and Culture Condition

K562 cells were from American Type Culture Collection (ATCC), (LGC Standards GmbH, and Germany) and BaF3 FLT3-ITD cells were a kind gift from Prof. Carol Stocking (University Hospital Hamburg-Eppendorf). Both suspension cells were cultured in RPMI media supplemented with 10% Fetal Calf serum (FCS). COS-7, HeLa and HT29 were from ATCC and were cultured in DMEM media supplemented with 10% FCS. Cells were incubated at 37° C., 5% $CO_2$ atmosphere. Compounds used for in vitro experiments were dissolved in DMSO (vehicle control) and diluted to a final concentration of 0.1% DMSO.

Antibodies

STAT3 (sc-482), phospho-STAT3 (sc-7993), STAT5 (se-835) and Bcl-xL (se-8392) were obtained from Santa Cruz Biotechnology (Santa Cruz, Calif.). Antibodies recognizing Cyclin D1 (2978), FLT3 (3462), phospho-STAT5 (9351), phospho-FLT3 (3461) were obtained from Cell Signaling Technology (Danvers, Mass.). Antibody to Pim1 (M08) was from Abnova (Taiwan) and Antibody to Beta actin (ab8227) was from Abcam (Cambridge, Mass.).

Cell Proliferation Assay

The effect of compounds on cell lines was evaluated by In Vitro Toxicology Assay Kit, Resazurin based with indicator dye Alamar Blue (Sigma). Adherent and suspension cells were plated at $5 \times 10^3$ per well and $1 \times 10^4$ per well respectively in triplicate in 96-well plates and incubated in medium containing 10% FBS. For adherent cell, the complete medium was replaced after 24 hours and incubated with test medium containing vehicle control or serial concentration of compounds for 48 hours at 37° C. The remaining wells in the periphery of the microtiter well plate were added PBS and not used to avoid evaporation effects. Alamar Blue was then added, and all plates were incubated at 37° C., and a colorimetric change was measured according to the methods provided by the provided protocol.

Western Blot Analysis and Immunoprecipitation

Cells were seeded at $0.5 \times 10^6$ in 6 well plate and allowed to grow overnight followed by 6 hour incubation with test compounds (0.1% DMSO) before protein extraction with M-PER™ Mammalian Protein Extraction Reagent (Pierce) containing 1% (vol/vol) complete protease inhibitor cocktail (Roche Molecular Biochemicals) and 1% (vol/vol) phosphate inhibitor cocktail (Sigma). For Western blotting, 15 μg of protein from each sample were then separated on a 10% SDS-PAGE and transferred to a PVDF membrane. The blots were blocked with TBST buffer (20 mM Tris-HCl [pH 7.4], 140 mM sodium chloride, and 0.05% Tween 20) containing 5% BSA at room temperature for 1 hour, washed 3 times in TBST buffer, and incubated with primary antibody overnight at 4° C. The membranes were then incubated with HRP-conjugated secondary antibody at room temperature for 1 hour. The reaction products were detected using Syngene Pxi4 imager and quantified by Image J.

Preparation for Nuclear Extracts and Cytoplasmic Extracts

Nuclear extracts and cytoplasmic extracts were prepared from BaF3 FLT3-ITD cells using the Nuclear Extraction kit (Active Motif, Carlsbad, Calif., USA) according to the manufacturer's protocol.

Gel Shift Assay

A gel shift assay was conducted using a double-stranded, biotin-labeled oligonucleotide probe containing the consensus binding site for STAT5 (sense strand, 5'-AGATTTCTAGGAATTCAATCC-3'), using the Gelshift Chemiluminescent EMSA kit (Active Motif) according to the manufacturer's protocol. Protein-DNA complexes were resolved on a nondenaturing polyacrylamide gel, transferred to a positively charged nylon membrane, and cross-linked to a membrane using the UV-light cross-linker. After blocking, the membrane was incubated with blocking buffer containing streptavidin conjugated to HRP. After washing, protein-DNA complexes were detected using a chemi-luminescent substrate (Active Motif).

Quantitative Evaluation of Activated STAT5 by ELISA

STAT5 activity was determined in nuclear protein extracts (20 μg) by the TransAM STATs family kits from Active Motif (Carlsbad, Calif.). All assays were performed following the manufactory instruction after the nuclear protein extraction.

The invention claimed is:
1. Furazan-3-carboxylic acid derivative of Formula 1:

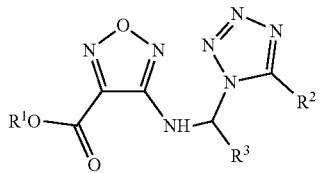

1 or a pharmaceutically acceptable salt thereof, wherein
$R^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and $[Q^1]_{m1}$-$L^1$;
$Q^1$ is a substituted or non-substituted bridging group selected from $C_1$-$C_{10}$-alkylene, $C_2$-$C_{10}$-alkenylene, $C_2$-$C_{10}$-alkynylene, —$CH_2O$—, —$CH(CH_3)O$—, —$CH_2CH_2O$—, —$CH_2CH_2CH_2O$—, —$CH(CH_3)CH_2O$—, and —$CH_2CH(CH_3)O$—;
m1 is an integer in the range of 1 to 10;
$L^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and —$C(O)CH_3$,
wherein in the above mentioned substituted groups one or more hydrogens are independently replaced by a substituent selected from deuterium, —F, —Cl, —Br, —I, and $C_1$-$C_6$-alkoxy;
$R^2$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{18}$-aryl, $C_5$-$C_{18}$-heteroaryl, and $[Q^2]_{m2}$-$Ar^1$-$[Q^3]_{m3}$-$[Ar^2]_{m4}$;
$Q^2$ is a substituted or non-substituted bridging group selected from $C_1$-$C_{10}$-alkylene, $C_2$-$C_{10}$-alkenylene, $C_2$-$C_{10}$-alkynylene, $C_6$-$C_{18}$-arylene, $C_5$-$C_{18}$-heteroarylene, —$(C_nH_{2n})O(C_nH_{2n})$—, —$(C_nH_{2n})NH(C_nH_{2n})$—, —$(C_nH_{2n})C(O)O(C_nH_{2n})$—, —$(C_nH_{2n})C(O)NH(C_nH_{2n})$—, and —$(C_nH_{2n})C(O)NHC(O)(C_nH_{2n})$—;
$Q^3$ is O or a substituted or non-substituted bridging group selected from $C_1$-$C_{10}$-alkylene, $C_2$-$C_{10}$-alkenylene, $C_2$-$C_{10}$-alkynylene, $C_6$-$C_{18}$-arylene, $C_5$-$C_{18}$-heteroarylene, —$O(C_nH_{2n})$—, —$(C_nH_{2n})O(C_nH_{2n})$—, —$(C_nH_{2n})NH(C_nH_{2n})$—, —$(C_nH_{2n})C(O)O(C_nH_{2n})$—, —$(C_nH_{2n})C(O)NH(C_nH_{2n})$—, and —$(C_nH_{2n})C(O)NHC(O)(C_nH_{2n})$—;
$Ar^1$ and $Ar^2$ are independently selected from a $C_6$-$C_{18}$-aryl group or a substituted $C_6$-$C_{18}$-aryl group, wherein one or more hydrogens are independently replaced by a substituent selected from deuterium, —F, —Cl, —Br, —I, —$C_nH_{2n+1}$, —$C_nF_{2n+1}$, —$O(C_nH_{2n+1})$, —$O(C_nF_2n+i)$, —OH, —$NH_2$, —$NH(C_nH_{2n+1})$, —$N(C_nH_{2n+1})_2$, —$NHS(O)_2C_nH_{2n-1}$, and —$N(C_nH_{2n+1})S(O)_2C_nH_{2n}$ 1;
m2 and m3 are independently from each other an integer in the range of 0 to 5;

m4 is 0 or 1;
n is an integer in the range of 1 to 5; and
$R^3$ is hydrogen or substituted or non-substituted $C_1$-$C_{10}$-alkyl,
with the proviso that $R^1$, $R^2$, and $R^3$ cannot simultaneously all be hydrogen.

2. The furazan-3-carboxylic acid derivative or pharmaceutically acceptable salt thereof of claim 1, wherein
$R^1$ is hydrogen or a substituted or non-substituted group selected from $C_1$-$C_4$-alkyl, $C_2$-$C_4$-alkenyl, $C_2$-$C_4$-alkynyl, $C_6$-$C_{12}$-aryl, $C_5$-$C_{12}$-heteroaryl, and $[Q^1]_{m1}$-$L^1$;
$Q^1$ is a substituted or non-substituted bridging group selected from $C_1$-$C_4$-alkylene, $C_2$-$C_4$-alkenylene, $C_2$-$C_4$-alkynylene, —$CH_2O$—, —$CH(CH_3)O$—, —$CH_2CH_2O$—, —$CH_2CH_2CH_2O$—, —$CH(CH_3)CH_2O$—, and —$CH_2CH(CH_3)O$—;
m1 is an integer in the range of 1 to 10;
$L^1$ is hydrogen or a substituted or non-substituted group selected from $C_1$-$C_{10}$-alkyl, $C_2$-$C_{10}$-alkenyl, $C_2$-$C_{10}$-alkynyl, $C_6$-$C_{15}$-aryl, $C_5$-$C_{18}$-heteroaryl, and —$C(O)CH_3$,
wherein in the above mentioned substituted groups one or more hydrogens are independently per Q replaced by a substituent selected from deuterium, —F, —Cl, —Br, —I, and $C_1$-$C_6$-alkoxy.

3. The furazan-3-carboxylic acid derivative or pharmaceutically acceptable salt thereof of claim 1, wherein $R^1$ represents hydrogen, methyl, n-butyl or —$CH(CH_3)OC(O)CH_3$.

4. The furazan-3-carboxylic acid derivative or pharmaceutically acceptable salt thereof of claim 1, wherein $R^2$ represents hydrogen or a substituted or non-substituted group selected from $C_6$-$C_{18}$-aryl, and $[Q^2]_{m2}$-$Ar^1$-$[Q^3]_{m3}$-$[Ar^2]_{m4}$;
$Q^2$ is a substituted or non-substituted bridging group selected from $C_1$-$C_4$-alkylene and —$(C_nH_{2n})NH(C_nH_{2n})$—;
$Q^3$ is O or —$O(C_nH_{2n})$—;
$Ar^1$ and $Ar^2$ are independently selected from a $C_6$-$C_{18}$-aryl group or a substituted $C_6$-$C_{18}$-aryl group, wherein one or more hydrogens are independently replaced by a substituent selected from —F, —Cl, —$C_nH_{2n+1}$, —$C_nF_{2n+1}$, —$O(C_nH_{2n+1})$, —$O(C_nF_2n+1)$, —OH, and —$NHS(O)_2C_nH_{2n-1}$;
m2, m3, and m4 are independently from each other 0 or 1;
n is an integer in the range of 1 to 4.

5. The furazan-3-carboxylic acid derivative or pharmaceutically acceptable salt thereof of claim 1, wherein $R^2$ represents hydrogen or a substituted or non-substituted group selected from $C_6$-$C_{10}$-aryl, and $[Q^2]_{m2}$-$Ar^1$-$[Q^3]_{m3}$-$[Ar^2]_{m4}$;
$Q^2$ is a substituted or non-substituted bridging group selected from $C_1$-$C_4$-alkylene and —$(C_nH_{2n})NH(C_nH_{2n})$—;
$Q^3$ is O or —$O(C_nH_{2n})$—;
$Ar^1$ and $Ar^2$ are independently selected from a $C_6$-$C_{10}$-aryl group or a substituted $C_6$-$C_{10}$-aryl group,
wherein one or more hydrogens are independently replaced by a substituent selected from —F, —Cl, —$C_nH_{2n+1}$, —$C_nF_{2n+1}$, —$O(C_nH_{2n+1})$, —$O(C_nF_{2n+1})$, —OH, and —$NHS(O)_2C_nH_{2n-1}$;
m2, m3, and m4 are independently from each other 0 or 1;
n is an integer in the range of 1 to 4.

6. The furazan-3-carboxylic acid derivative or pharmaceutically acceptable salt thereof of claim 1, wherein $R^2$ represents hydrogen or a substituted or non-substituted group selected from C₆-aryl, and $[Q^2]_{m2}$-$Ar^1$-$[Q^3]_{m3}$-$[Ar^2]_{m4}$;

Q² is a substituted or non-substituted bridging group selected from $C_1$-$C_4$-alkylene and —$(C_nH_{2n})NH(C_nH_{2n})$—;

Q³ is O or —$O(C_nH_{2n})$—;

Ar¹ and Ar² are independently selected from a C₆-aryl group or a substituted C₆-aryl group, wherein one or more hydrogens are independently replaced by a substituent selected from —F, —Cl, —$C_nH_{2n+1}$, —$C_nF_{2n+1}$, —$O(C_nH_{2n+1})$, —$O(C_nF_{2n+1})$, —OH, and —$NHS(O)_2C_nH_{2n-1}$;

m2, m3, and m4 are independently from each other 0 or 1;

n is an integer in the range of 1 to 4.

7. The furazan-3-carboxylic acid derivative or pharmaceutically acceptable salt thereof of claim 1, wherein R² represents hydrogen, phenyl or one of Formulae 2-1 to 2-22

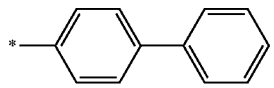  2-1

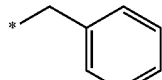  2-2

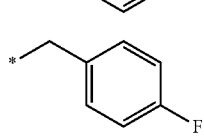  2-3

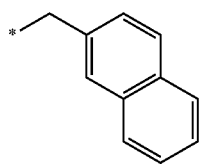  2-4

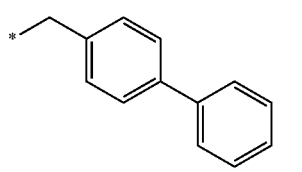  2-5

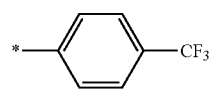  2-6

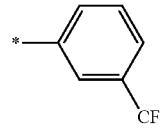  2-7

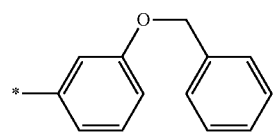  2-8

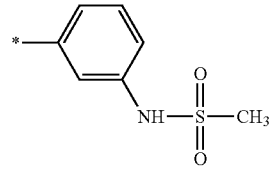  2-9

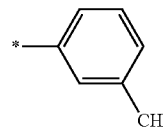  2-10

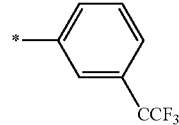  2-11

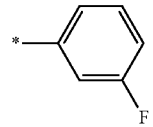  2-12

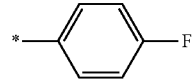  2-13

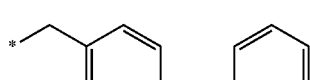  2-14

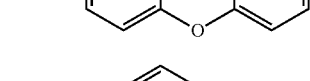  2-15

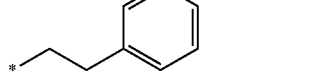  2-16

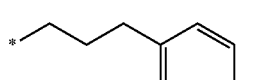  2-17

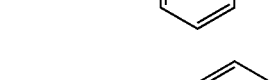  2-18

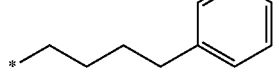  2-19

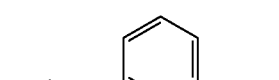  2-20

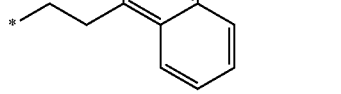  2-21

-continued

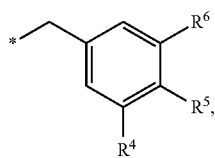

wherein $R^4$ is —OH, —F, or —Cl;
$R^5$ is —OCH$_3$, —OCF$_3$, or —CH$_3$;
$R^6$ is —OH, —F, or —Cl.

8. The furazan-3-carboxylic acid derivative or pharmaceutically acceptable salt thereof of claim 1, wherein $R^3$ is hydrogen, or substituted or non-substituted $C_1$-$C_4$-alkyl.

9. The furazan-3-carboxylic acid derivative or pharmaceutically acceptable salt thereof of claim 1, wherein $R^1$ and $R^3$ are hydrogen.

10. The furazan-3-carboxylic acid derivative or pharmaceutically acceptable salt thereof of claim 1, wherein $R^3$ is one of hydrogen, methyl, or n-butyl.

11. The furazan-3-carboxylic acid derivative or pharmaceutically acceptable salt thereof of claim 1, wherein the furazan-3-carboxylic acid derivative is represented by of one of Formulae 6, 7, 15 to 21, 23 to 41 as well as 100, 104, 108, 113, 169, 173, 174, 177, 178 and 196:

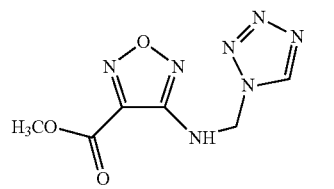

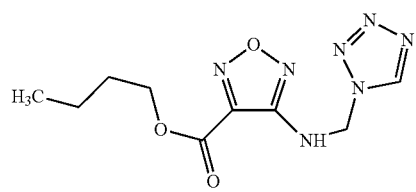

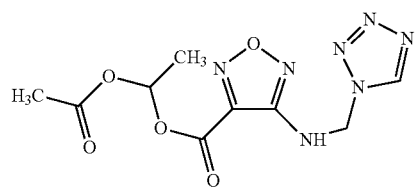

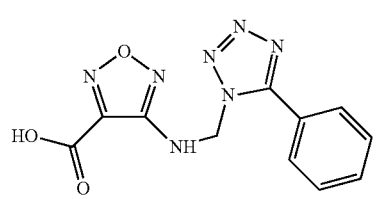

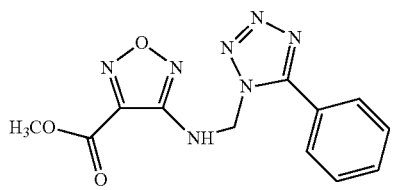

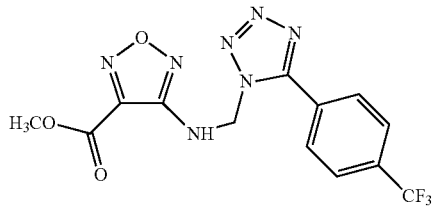

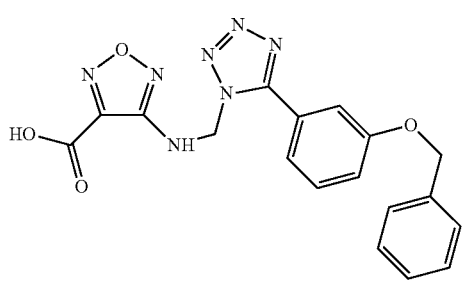

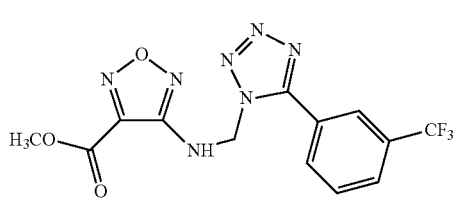

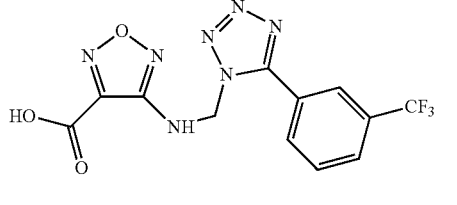

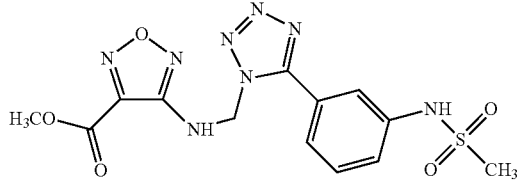

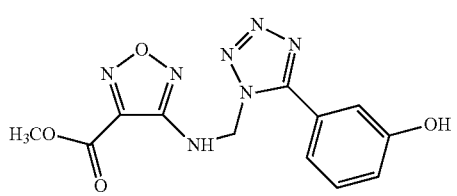

25
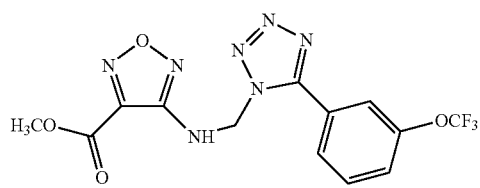
26
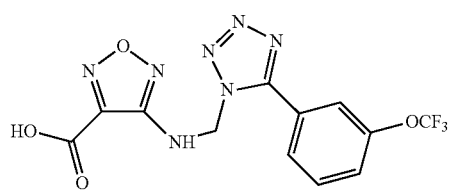
27
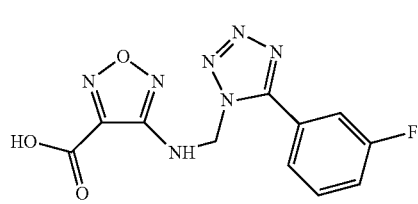
28
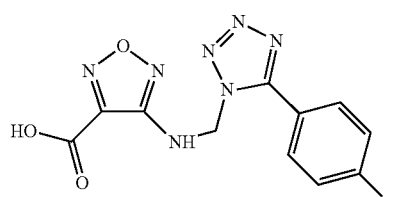
29
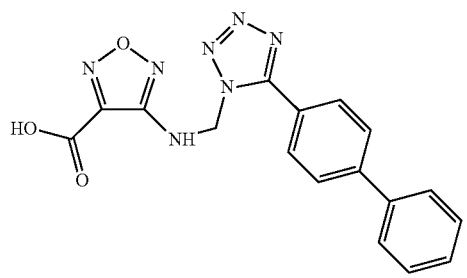
30
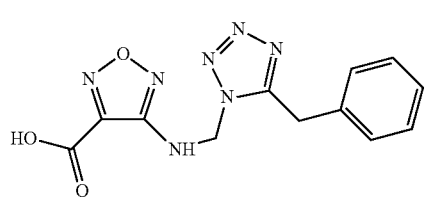
31
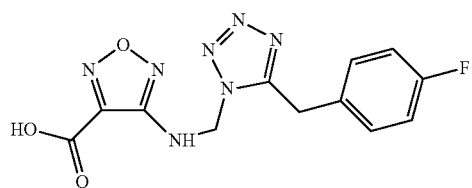
32
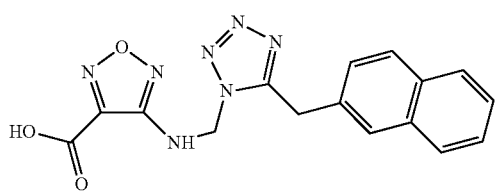
33
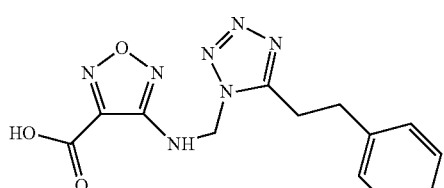
34
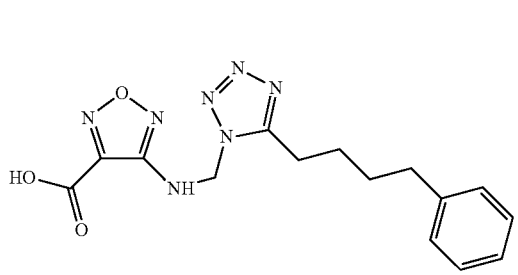
35
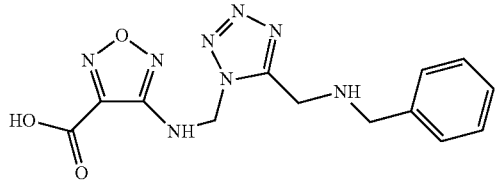
36
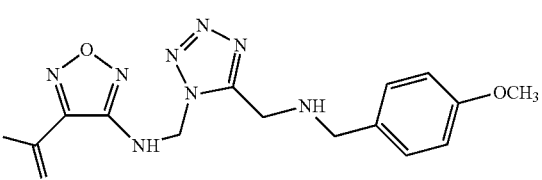
37
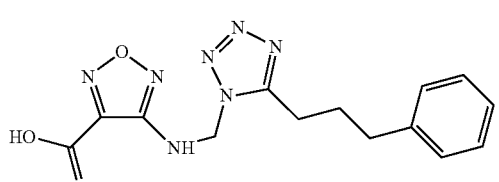
38
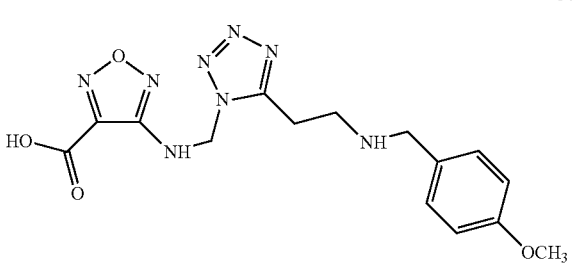

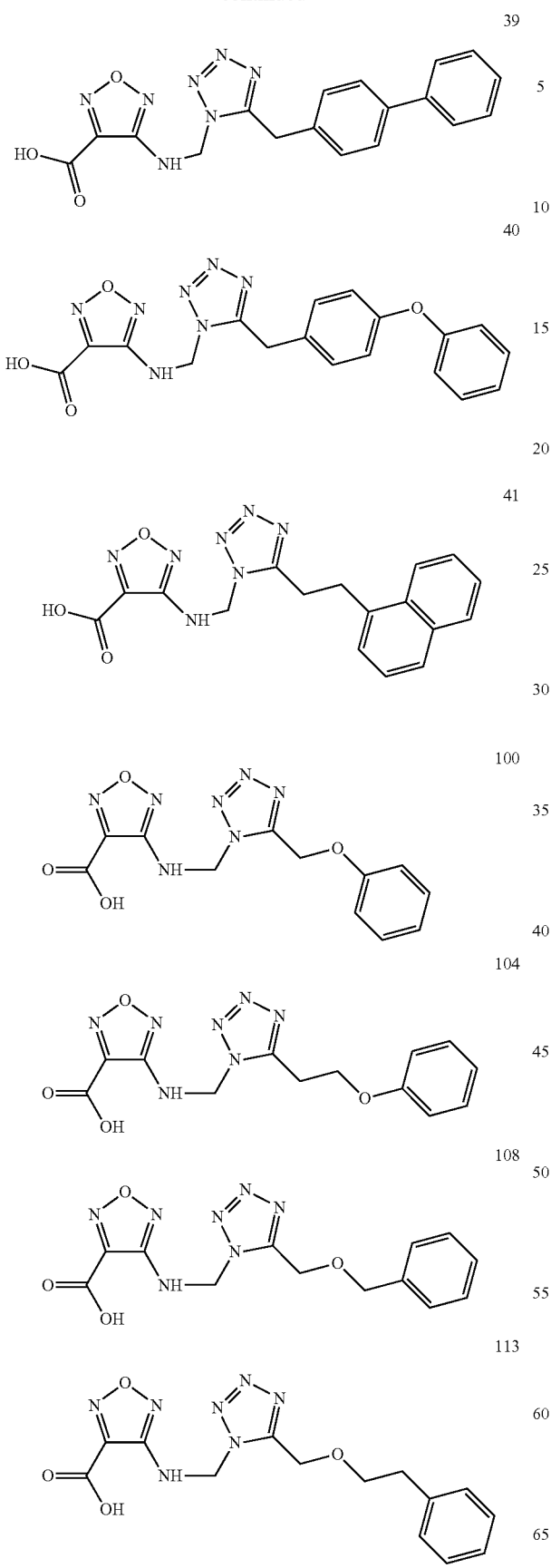

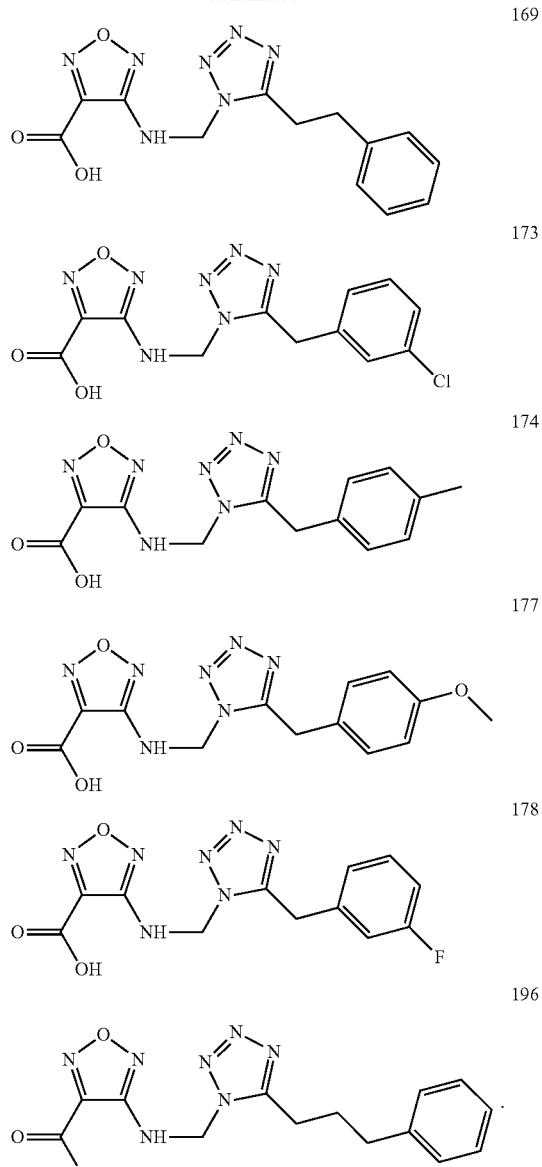

12. The furazan-3-carboxylic acid derivative or pharmaceutically acceptable salt thereof of claim 1 for use in reversing, alleviating or inhibiting progression of cancer associated with increased STAT5 signaling.

13. A furazan-3-carboxylic acid derivative of Formula 3

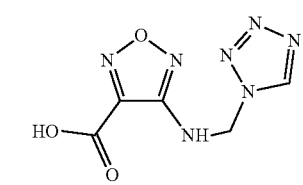 [SMILES: O=C(O)c1nonc1NCn1cnnn1]

or pharmaceutically acceptable salt thereof for use in treatment of cancer associated with increased STAT5 signaling.

14. A pharmaceutical composition comprising a furazan-3-carboxylic acid derivative or pharmaceutically acceptable salt thereof of claim 1 as an active ingredient and, optionally, one or more pharmaceutically acceptable excipients.

15. The pharmaceutical composition according to claim 14, further comprising at least one anticancer agent selected from a group consisting of a JAK inhibitor, a BCR-ABL inhibitor, a FLT3 inhibitor, and a PI3K inhibitor.

16. The furazan-3-carboxylic acid derivative of Formula 3 of claim 13, wherein the cancer is selected from the group consisting of: leukemia, chronic myeloid leukemia and acute myeloid leukemia.

* * * * *